(12) United States Patent
Tusé et al.

(10) Patent No.: US 6,169,104 B1
(45) Date of Patent: Jan. 2, 2001

(54) DI-ARYL ETHERS AND THEIR DERIVATIVES AS ANTI-CANCER AGENTS

(75) Inventors: Daniel Tusé, Menlo Park; Xiaoying Chen, Newark; Charles K. Hiebert, Sunnyvale; Cris M. Olsen, Soquel; Keith Laderoute; Nahid Waleh, both of Palo Alto; A. Merrill Knapp, Menlo Park, all of CA (US)

(73) Assignees: Large Scale Biology Corporation, Vacaville; SRI International, Menlo Park, both of CA (US)

( * ) Notice: Under 35 U.S.C. 154(b), the term of this patent shall be extended for 0 days.

(21) Appl. No.: 09/047,945

(22) Filed: Mar. 25, 1998

Related U.S. Application Data
(60) Provisional application No. 60/041,679, filed on Mar. 26, 1997.

(51) Int. Cl.$^7$ .................................................. A61K 31/415
(52) U.S. Cl. ............................................................ 514/405
(58) Field of Search ............................................ 514/405

(56) References Cited

U.S. PATENT DOCUMENTS

| | | | |
|---|---|---|---|
| 5,284,865 | 2/1994 | Holton et al. | 514/449 |
| 5,356,928 | 10/1994 | Murray et al. | 514/449 |
| 5,430,062 | 7/1995 | Cushman et al. | 514/646 |
| 5,504,074 | 4/1996 | D'Amato et al. | 514/182 |
| 5,571,822 | 11/1996 | Lee et al. | 514/312 |
| 5,587,459 | 12/1996 | Uckun | 530/391.1 |
| 5,736,576 | 4/1998 | Kun et al. | 514/570 |

FOREIGN PATENT DOCUMENTS

WO 93/24442  12/1993  (WO).

OTHER PUBLICATIONS

Folkman, "Fighting Cancer by Attacking Its Blood Supply," *Scientific American*, pp. 150–154, Sep. 1996.

*Primary Examiner*—Kevin E. Weddington
(74) *Attorney, Agent, or Firm*—Townsend and Townsend and Crew LLP

(57) ABSTRACT

The present invention relates, inter alia, to compounds that bind tubulin and exhibit anti-mitotic properties and to methods of using such compounds to inhibit abnormal cell mitosis and, in particular, to inhibit tumor cell growth. In addition, methods are presented of treating mammalian diseases associated with undesired and uncontrolled angiogenesis.

26 Claims, 2 Drawing Sheets

DI-ARYL ETHERS AND THEIR DERIVATIVES AS ANTI-CANCER AGENTS

This application is a continuation-in-part of U.S. Provisional Patent Application Ser. No. 60/041,679, filed Mar. 26, 1997, the teachings of which are incorporated herein by reference. This application is also related to co-pending, commonly assigned U.S. Provisional Patent Application Ser. No. 60/079,313, filed on even date herewith, the teachings of which are incorporated herein by reference.

BACKGROUND OF THE INVENTION

Cell mitosis is a multi-step process that includes cell division and replication (Alberts, B., et al., In The Cell, pp. 652–661 (1989); Stryer, E. Biochemistry (1988)). Mitosis is characterized by the intracellular movement and segregation of organelles, including mitotic spindles and chromosomes. Organelle movement and segregation are facilitated by the polymerization of the cell protein tubulin. Microtubules are formed from alpha and beta tubulin polymerization and the hydrolysis of guanosine triphosphate (GTP). Microtubule formation is important for cell mitosis, cell locomotion and the movement of highly specialized cell structures such as cilia and flagella.

Unfortunately, numerous diseases are characterized by abnormal cell mitosis. For example, uncontrolled cell mitosis is a hallmark of cancer. Cancer is the leading cause of death, second only to heart disease, of both men and women. In the fight against cancer, numerous techniques have been developed and are the subject of current research directed to understanding the nature and cause of the disease and to providing methods for the control or cure thereof.

To date, three major families of antitumor agents are known. Each of the families of agents is associated with a recognized mechanism of action. First, antitumor agents may be alkylating agents, which generally bind in a covalent manner with DNA to form bifunctional lesions. The bifunctional lesions involve adjacent or nearby bases of the same strand or, alternatively, involve bases on opposite strands forming interstrand crosslinks. Examples of alkylating agents include nitrogen mustard, cyclophosphamide and chlorambucil. Toxicities associated with the use of alkylating agents include nausea, vomiting, alopecia, hemorrhagic cystitis, pulmonary fibrosis, etc. Second, antitumor agents may be antimetabolites, which generally inhibit enzymes involved in the synthesis or assembly of DNA. Alternatively, an antimetabolite may serve as a fraudulent or analog substrate of DNA processes. Examples of antimetabolites include purine, pyrimidine and folate antagonists and plant alkaloids such as vincristine and vinblastine. Toxicities associated with the use of antimetabolites include alopecia, myelosuppression, vomiting, nausea, peripheral neuropathy, etc. Third, antitumor agents may be antibiotics, which work by intercalating into the DNA helix or introducing strand breaks into DNA. Examples of antibiotics include doxorubicin, daunorubicin and actinomycin. Toxicities associated with the use of antibiotics include myelosuppression, anaphylactic reactions, anorexia, cardiotoxicity, pulmonary fibrosis, etc.

Ionizing radiation is a well established treatment for malignant disease and is of proven benefit for both curative and palliative purposes. However, radiotherapy can have several undesirable complications, such as mucositis, leukopenia, desquamation, spinal cord necrosis, and oblitterative endarteritis. These complications frequently limit the ability to deliver a full therapeutic dose of radiation or cause significant morbidity following treatment. Many chemotherapy agents are also toxic to cells of normal tissue, and, thus, the side-effects of chemotherapy are sometimes almost as devastating to the patient as the tumor burden itself. One approach to reducing the side effects of chemotherapy has been to attempt to target chemotherapeutic agents, including radioisotopes and various plant and bacterial toxins, to tumor cells by attaching the agents to antibodies that are specific for antigens present on a tumor cell. See, e.g., U.S. Pat. Nos. 4,348,376 and 4,460,559 which describe radioimmunotherapy of solid tumors (carcinomas) using an anti-carcinoembryonic antigen antibody, and U.S. Pat. No. 5,595,721 which is directed to radioimmunotherapy of lymphoma, a more disseminated tumor. However, while there are several reports of individual successes, the results of therapy using antibody conjugates has generally been disappointing. Remission rates have been low and generally non-reproducible.

Although thousands of potential anticancer agents have been evaluated, the treatment of human cancer remains fraught with complications which often present an array of suboptimnal treatment choices. As such, chemotherapeutic agents which possess little or no toxicity, which are inexpensive to obtain or manufacture, which are well tolerated by the patient, and which are easily administered would be a desirable addition to the therapeutic modalities currently available to the oncologist. Agents that will selectively sensitize malignant tissue to allow lower doses of radiation or therapy to achieve the same therapeutic effect with less damage to healthy tissues are also desirable. Similarly, agents that prevent cancer from occurring or reoccurring are also desirable. The present invention remedies these needs by providing such chemotherapeutic and sensitizing agents.

SUMMARY OF THE INVENTION

The present invention relates to (i) compounds that bind tubulin and exhibit anti-mitotic properties, (ii) methods of using such compounds to inhibit abnormal cell mitosis and, in particular, to inhibit tumor cell growth, (ii) compounds that inhibit angeogenesis and the vascularization of endothelial cells, (iv) methods of using such compounds to inhibit angiogenesis and the vascularization of endothelial cells, (v) compounds that reduce the level of tumor necrosis factor α (TNF-α) produced by a cell; (vi) methods of using such compounds to reduce TNF-α production and to treat inflammatory diseases; and (vii) pharmaceutical compositions comprising such compounds.

In one embodiment, the present invention provides compounds having the general formula:

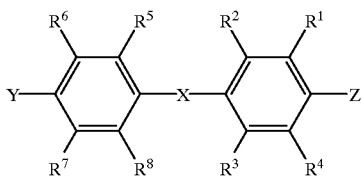

I or a pharmaceutically acceptable salt thereof.

In Formula I, $R^1$, $R^2$, $R^3$ and $R^4$ are each independently selected and are functional groups including, but not limited to, H, alkyl, S-alkyl, alkenyl, alkynyl, aryl, hydroxyl, alkoxy, halogen, $NO_2$ and $NH_2$. $R^5$, $R^6$, $R^7$ and $R^8$ are each independently selected and are functional groups including, but not limited to, H, S-alkyl, alkyl, alkenyl, alkynyl, aryl, hydroxyl, alkoxy and halogen.

In Formula I, X, if present, is a group including, but not limited to, the following:

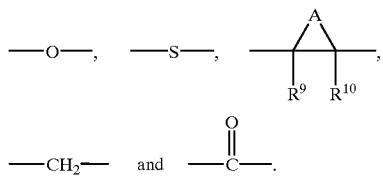

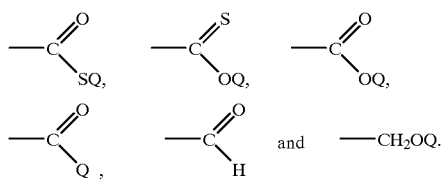

A, in the above formula, together with the carbons to which it is bound, forms an optionally substituted 3, 4, 5 or 6 membered carbocylic or heterocyclic ring. $R^9$ and $R^{10}$ in the above formula are independently hydrogen, alkyl and halogen. Y, in Formula I, is a functional group including, but not limited to, H, alkyl and alkoxy. Z is a functional group including, but not limited to, the following:

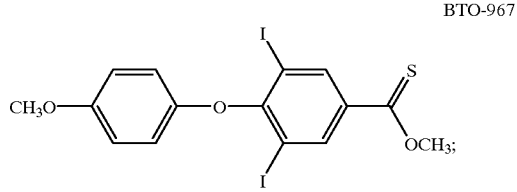

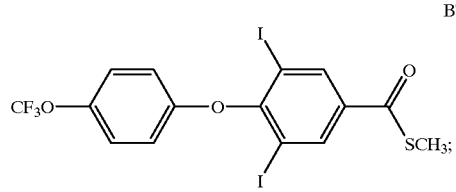

Q, in the above formula Z, is a functional group including, but not limited to, H, alkyl and S-alkyl. Z, Q and Y are selected such that if Z is

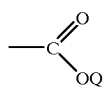

and Q is methyl, then Y is other than methoxy and ethoxy.

Within the scope of Formula I, certain embodiments are preferred. Examples of particularly preferred compounds include, but are not limited to, those compounds set forth below. The compounds set forth below and throughout this specification are referred to by code numbers, which are used for convenience only, and are strictly arbitrary for purposes of this invention.

BTO-967

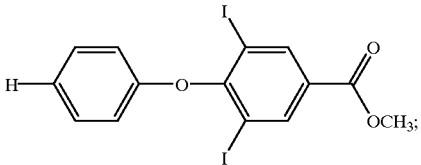

BTO-969

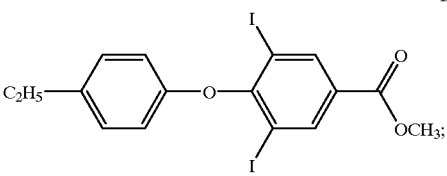

BTO-990

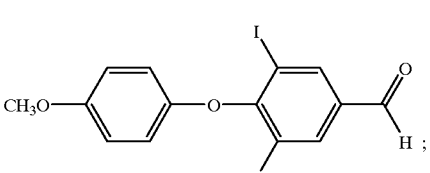

BTO-971

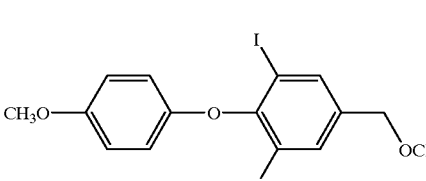

BTO-964

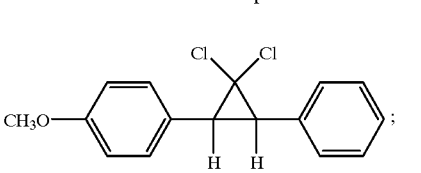

BTO-966

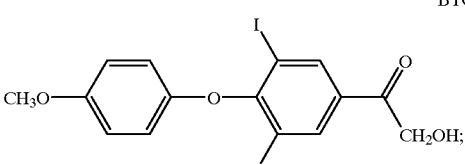

BTO-980

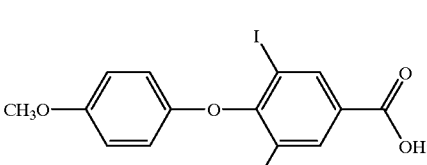

BTO-972

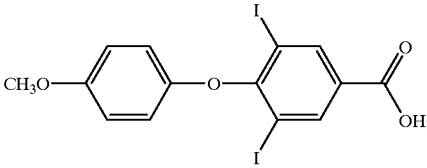

BTO-985 and

BTO-986

The compounds of the present invention can be used either in vivo or in vitro to inhibit the growth of a tumor cell. The compounds of the present invention are also useful because they bind tublin and exhibit antimitotic properties and, thus, can be used either in vivo or in vitro to inhibit abnormal cell mitosis. Moreover, the compounds of the present invention are useful because they inhibit angiogenesis and the vascularization of endothelial cells. In addition, the compounds of the recent invention are useful because they reduce (e.g., downregulate) the level of TNF-α produced by a cell.

The compounds of the present invention also are useful in conjunction with other cancer therapies, including radiation therapy, chemotherapy, and immunotherapy (including radioimmunotherapy). Within these embodiments, the compounds of the present invention are particularly useful as sensitizing agents. When administered prior to, simultaneously with, or after treatment with a cancer therapy, the compounds of the invention increase the sensitivity of cancer cells to the therapy. This results not only in an increase in effectiveness of the therapy, but also can reduce the dosage required, thereby reducing undesirable side effects. It has been discovered that the compounds of the present invention are safe, effective, non-toxic and easy to administer.

As such, in one embodiment, the present invention provides a method of inhibiting the growth of a tumor cell, the method comprising contacting the tumor cell with a compound having the general formula:

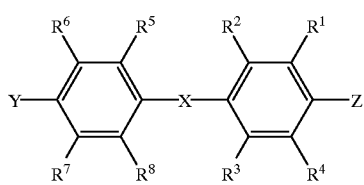

I or a pharmaceutically acceptable salt thereof.

In another embodiment, the present invention provides a method of treating cancer, the method comprising administering to a mammalian subject having cancer a therapeutically effective amount of a compound having the general formula:

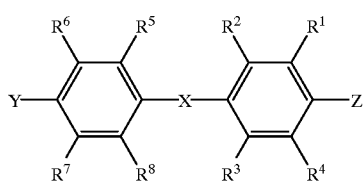

I or a pharmaceutically acceptable salt thereof.

The compounds of the present invention are useful for inhibiting the growth of a number of tumor cells and for treating a wide variety of cancers. Such tumor cells include, by way of example and not limitation, lung, colon, breast, ovarian, prostate and hepatic tumor cells as well as squamous cell carcinomas. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas. Moreover, in accordance with the above methods, mammalian subjects include, but are not limited to, humans, laboratory animals, domestic pets and farm animals. In addition, it will be readily apparent to those of skill that using the compounds of Formula I, the growth of tumor cells can be inherited in other higher order organisms including, but not limited to, plants, insects, fish and the like.

In yet another embodiment, the present invention provides a method of treating a disease characterized by abnormal cell mitosis, the method comprising administering to a mammalian subject having such a disease a therapeutically effective amount of a compound having the general formula:

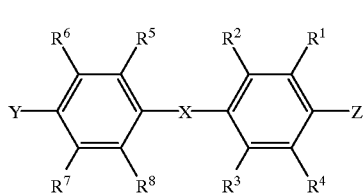

I or a pharmaceutically acceptable salt thereof.

The present invention also provides methods of treating a mammal afflicted with a disease characterized by abnormal cell mitosis and, in particular, tumor cell growth by administering to the mammal an effective amount of ionizing or nonionizing radiation, or an effective amount of a chemotherapeutic or immunotherapeutic agent, in conjunction with an effective sensitizing amount of a compound of Formula I. The compounds enhance the deleterious cellular effects of exposure to ionizing radiation or to a chemotherapeutic or immunotherapeutic agent inflicted on cells undergoing abnormal cell mitosis. Such effects include, for example, damage to cellular DNA, such as DNA strand breaks, disruption in cellular function, such as by disrupting DNA function, cell death and the like.

In addition to the foregoing, the compound of the present invention can be used in conjunctive therapy with other known chemotherapeutic or antineoplastic agents (e.g., vinca alkaloids, antibiotics, antimetabolites, platinum coordination complexes, etc.). For instance, the compounds of the present invention can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; and a platinum coordination complex, such as cisplatin (cis-DDP), carboplatin, etc. In addition, those of skill in the art will appreciate that the compounds of the present invention can be used in conjunctive therapy with other known chemotherapeutic or antineoplastic compounds.

In another aspect, this invention relates to a method of inhibiting the vascularization of endothelial cells, the method involves contacting a cell, tissue or organ which has endothelial cells, with an anti-angiogenic amount of a compound of Formula I or a pharmaceutically acceptable salt thereof.

In another aspect, this invention relates to a method for effectively inhibiting unwanted angiogenesis in a tissue or organ, by administering to the mammal a compound of Formula I, or a pharmaceutical composition thereof, in a dosage sufficient to inhibit angiogenesis.

Also provided by the invention are methods of preventing a disease characterized by abnormal cell mitosis. By administering a compound of Formula I to a mammal that is or could be susceptible to such diseases, the development of abnormal mitosis can be prevented. Similarly, the present invention provides methods of preventing a disease characterized by abnormal cell mitosis from reoccurring.

In still another aspect, the present invention provides a method of reducing the level of tumor necrosis factor α (TNF-α) produced by a cell. As a result of their ability to reduce TNF-α, the compounds of Formula I are particularly useful for treating inflammatory diseases.

Other features, objects and advantages of the invention and its preferred embodiments will become apparent from the detailed description which follows.

DETAILED DESCRIPTION OF THE INVENTION AND PREFERRED EMBODIMENTS

Figure 1:
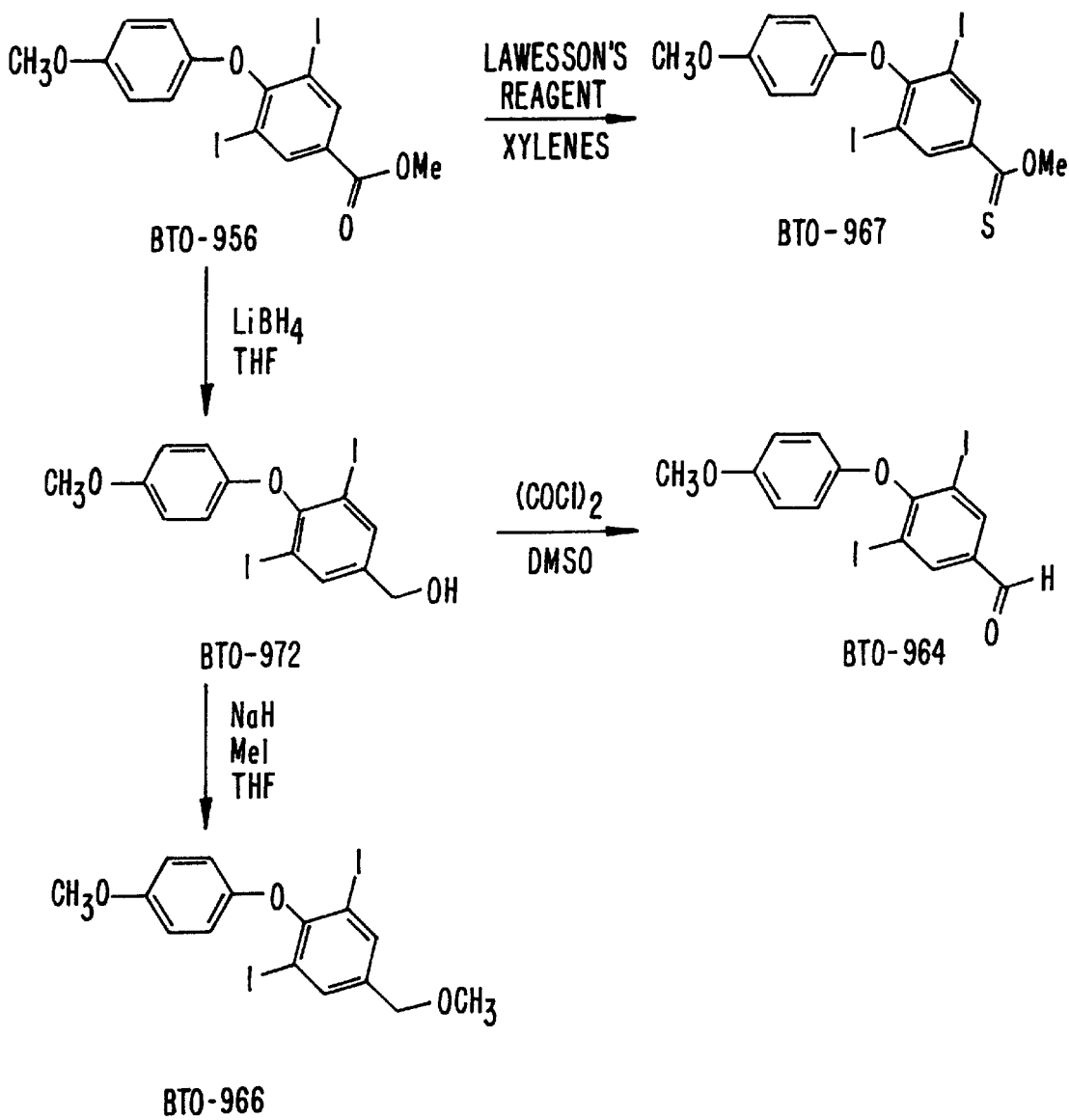
FIG. 1 illustrates the synthetic schemes that can be used to prepare the compounds of the present invention.
Figure 2A:
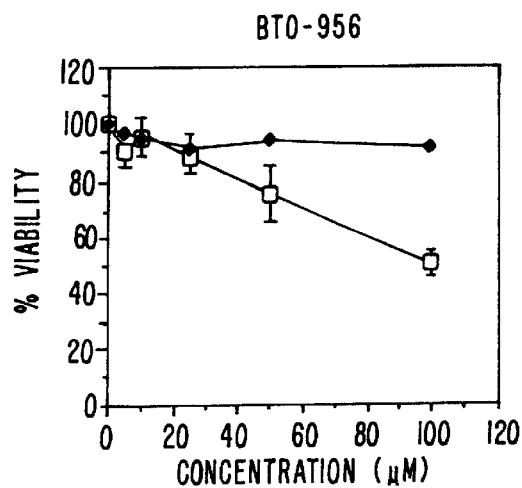
FIG. 2 illustrates the in vitro metabolism of BTO-956, 964, 966, and 967 in human leukemia cells. In this experiments, human leukemia cells (HL60) were incubated for 4 hours in the presence of BTO-956, BTO-964, BTO-966 or BTO-967, with (closed symbols) and without (open symbols) rat liver microsome fraction S9. Following the 4 hr exposure to drug and S9, the cells were rinsed and replated at a density of $2\times10^5$ cells per ml, and counted 3 days later.
Figure 2B:
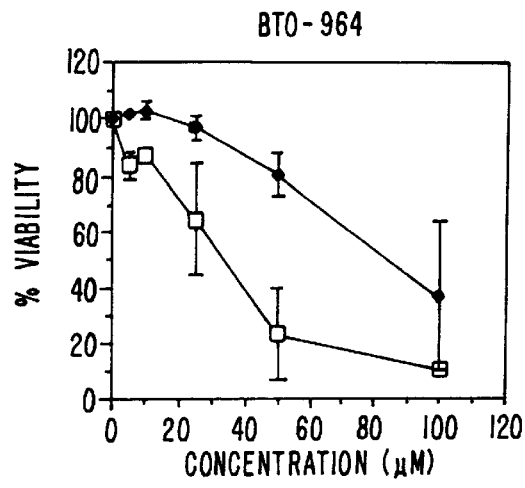
Figure 2C:
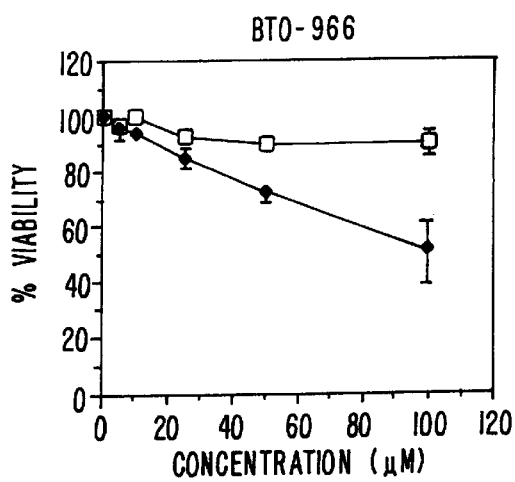
Figure 2D:
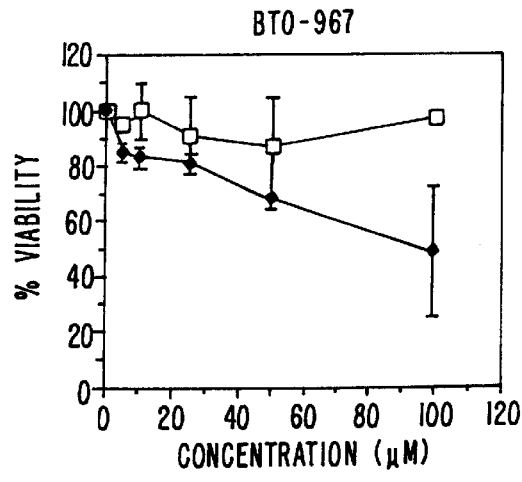

The present invention relates to (i) compounds that bind tubulin and exhibit anti-mitotic properties, (ii) methods of using such compounds to inhibit abnormal cell mitosis and, in particular, to inhibit tumor cell growth, (iii) compounds that inhibit angeogenesis and the vascularization of endothelial cells, (iv) methods of using such compounds to inhibit angiogenesis and the vascularization of endothelial cells, (v) compounds that reduce the level of tumor necrosis factor α (TNF-α) produced by a cell; (vi) methods of using such compounds to reduce TNF-α production and to treat inflammatory diseases; and (vii) pharmaceutical compositions comprising such compounds.

A. DEFINITIONS

The term "independently selected" is used herein to indicate that the R groups, e.g., $R^1$, $R^2$, $R^3$ and $R^4$, can be identical or different (e.g., $R^1$, $R^2$, $R^3$ and $R^4$ may all be hydrogens or $R^1$ and $R^4$ may be hydrogen and $R^2$ and $R^3$ may be halogen, etc.).

The term "alkyl" is used herein to refer to a branched or unbranched, saturated or unsaturated, monovalent hydrocarbon radical having from 1–12 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "S-alkyl" is used herein to refer to the group —SR, where R is lower alkyl or substituted lower alkyl as defined herein.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "halogen" is used herein to refer to fluorine, bromine, chlorine and iodine atoms.

The term "hydroxy" is used herein to refer to the group —OH.

The term "amino" is used to refer to the group —NRR', where R and R' may independently be hydrogen, alkyl, substituted alkyl, aryl, substituted aryl or acyl.

The term "nitro" is used herein to refer to the group —$NO_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkenyl" is used herein to refer to an unsaturated branched, straight chain or cyclic monovalent hydrocarbon radical having at least one carbon—carbon double bonds. The radical can be in either the cis or trans conformation about the double bond(s). Suitable alkenyl radicals include, for example, ethenyl, propenyl, isopropenyl, cyclopropenyl, butenyl, isobutenyl, cyclobutenyl, tert-butenyl, pentenyl, hexenyl, etc.

The term "carbocyclic" is used herein to refer to a non-aromatic carbon ring structure. This may include cyclopropane, cyclobutane, cyclopentane, cyclohexane and the like. The carbocyclic ring may be optionally substituted with one or more functional groups such as alkyl, halogen, hydroxy, amino, alkoxy, hydroxyalkyl and the like.

The term "heterocyclic" is used herein to refer to aromatic and non-aromatic ring structures containing at least one heteroatom. This includes oxacyclopropane, azacyclopropane, thiophene, furan, pyrrole, imidazole, pyridine and the like.

The term "alkynyl" is used herein to refer to an unsaturated branched, straight chain or cyclic monovalent hydrocarbon radical having at least one carbon—carbon triple bond. Suitable alkynyl radicals include, for example, ethynyl, propynyl, butynyl, isobutynyl, pentynyl, hexynyl, etc.

The term "angiogenesis" refers to the generation of new blood vessels into tissue, organs or tumors.

The term "contacting" is used herein interchangeably with the following: combined with, added to, mixed with, passed over, incubated with, Rowed over, etc. Moreover, the compounds of present invention can be "administered" by any conventional method such as, for example, parenteral, oral, topical and inhalation routes as described herein.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, ptoluenesulfonic acid, salicylic acid and the like. Pharmaceutically acceptable salts include, for example, alkali metal salts, such as sodium and potassium, alkaline earth salts and ammonium salts.

"An amount sufficient," "an effective amount" or "therapeutically effective amount" refer to an amount of a compound or composition effective to depress, suppress or regress malignant cell growth or result in amelioration of symptoms associated with cancerous diseases. The desired result can be either a subjective relief of a symptom(s) or an objectively identifiable improvement in the recipient of the dosage, a decrease in tumor size, a decrease in the rate of growth of cancer cells as noted by the clinician or other qualified observer.

The term "anti-angeogenic" amount refer to an amount of a compound or composition effective to depress, suppress or inhibit angiogenesis or result in amelioration of symptoms associated with angiogenic diseases.

The term "sensitization enhancement ratio" (SER) refers to the ratio of the radiation dose, chemotherapeutic agent dose or inmunotherapeutic agent dose required to reduce the survival fraction of cancer cells to a predetermined level (e.g., 1% of the control) compared to the dose required to attain the same survival fraction with a sensitizer present. An "effective sensitizing amount" is that amount of compound that is effective, upon single or multiple dose administration to a cell, in enhancing the severity or extent the deleterious cellular effects to cancer cells caused by exposure to or treatment with ionizing or nonionizing radiation, a chemotherapeutic agent or an immunotherapeutic agent.

The terms "treating cancer," "therapy," and the like refer generally to any improvement in the mammal having the cancer wherein the improvement can be ascribed to treatment with the compounds of the present invention. The improvement can be either subjective or objective. For example, if the mammal is human, the patient may note improved vigor or vitality or decreased pain as subjective symptoms of improvement or response to therapy. Alternatively, the clinician may notice decrease in tumor size or tumor burden based on physical exam, laboratory parameters, tumor markers or radiographic findings. Some laboratory signs that the clinician may observe for response to therapy include normalization of tests such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement such as sonograms, nuclear magnetic resonance testing and positron emissions testing.

"Inhibiting the growth of tumor cells" can be evaluated by any accepted method of measuring whether growth of the tumor cells has been slowed or diminished. This includes direct observation and indirect evaluation such as subjective symptoms or objective signs as discussed above.

B. THE COMPOUNDS

The present invention provides compounds that, inter alia, inhibit tumor cell growth. Moreover, the compounds of the present invention bind tubulin and exhibit anti-mitotic properties. In addition, the compounds of the present invention inhibit angiogenesis and the vascularization of endothelial cells. As a result of their properties, the compounds of the present invention can be used, inter alia, to inhibit tumor cell growth, to inhibit abnormal cell mitosis and to inhibit angiogenesis. In one embodiment, the present invention provides compounds having the general formula:

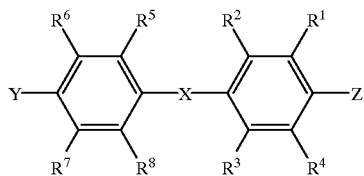

or a pharmaceutically acceptable salt thereof.

In Formula I, $R^1$, $R^2$, $R^3$ and $R^4$ are each independently selected and are functional groups including, but not limited to, H, alkyl, S-alkyl, alkenyl, alkynyl, aryl, hydroxyl, alkoxy, halogen, $NO_2$ and $NH_2$. $R^5$, $R^6$, $R^7$ and $R^8$ are each independently selected and are functional groups including, but not limited to, H, alkyl, S-alkyl, alkenyl, alkynyl, aryl, hydroxyl, alkoxy and halogen.

In Formula I, X, if present, is a functional group including, but not limited to, the following:

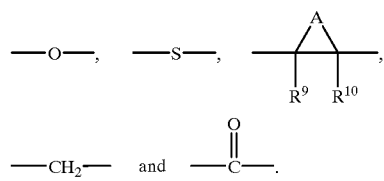

A, in the above formula, together with the carbons to which it is bound forms an optionally substituted 3, 4, 5 or 6 membered carbocyclic or heterocyclic ring. $R^9$ and $R^{10}$ in the above formula are independently hydrogen, alkyl and halogen. Y, in Formula I, is a functional group including, but not limited to, H, alkyl and alkoxy. Z is a functional group including, but not limited to, the following:

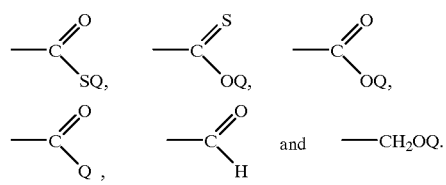

Q, in the above formula Z, is a functional group including, but not limited to, H, alkyl and S-alkyl. Z, Q and Y are selected such that if Z is

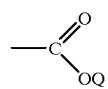

and Q is methyl, then Y is other than methoxy and ethoxy.

Within the scope of the above Formula I, certain embodiments are preferred. In Formula I, one preferred embodiment is that in which X is —O—; Y is methoxy; Z is

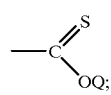

Q is methyl; $R^1$ and $R^4$ are both hydrogen; $R^2$ and $R^3$ are both iodo; and $R^5$, $R^6$, $R^7$ and $R^8$ are all hydrogen. Another preferred embodiment is that in which X is —O—; Y is hydrogen; Z is

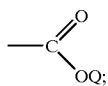

Q is methyl; $R^1$ and $R^4$ are both hydrogen; $R^2$ and $R^3$ are both iodo; and $R^5$, $R^6$, $R^7$ and $R^8$ are all hydrogen. Another preferred embodiment is that in which X is —O—; Y is alkyl; Z is

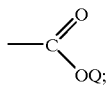

Q is methyl; $R^1$ and $R^4$ are both hydrogen; $R^2$ and $R^3$ are both iodo; and $R^5$, $R^6$, $R^7$ and $R^8$ are all hydrogen. Yet another preferred embodiment is that in which X is —O—; Y is methoxy; Z is

$R^1$ and $R^4$ are both hydrogen; $R^2$ and $R^3$ are both iodo; and $R^5$, $R^6$, $R^7$ and $R^8$ are all hydrogen. Still another preferred embodiment is that in which X is —O—; Y is methoxy; Z is —CH$_2$OQ; Q is hydrogen; $R^1$ and $R^4$ are both hydrogen; $R^2$ and $R^3$ are both iodo; and $R^5$, $R^6$, $R^7$ and $R^8$ are all hydrogen. Still yet another preferred embodiment is that in which X is —O—; Y is methoxy; Z is —CH$_2$OQ; Q is methyl; $R^1$ and $R^4$ are both hydrogen; $R^2$ and $R^3$ are both iodo; and $R^5$, $R^6$, $R^7$ and $R^8$ are all hydrogen.

The following is a list of compounds in accordance with the present invention which are particularly preferred.

BTO-967
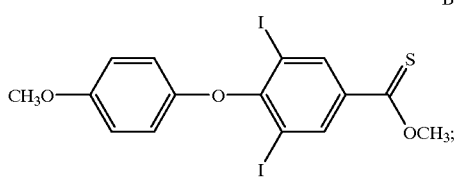

BTO-969
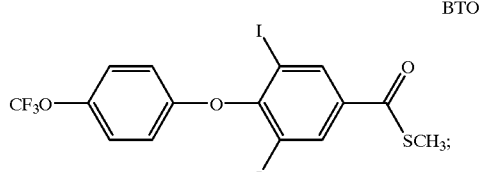

BTO-990
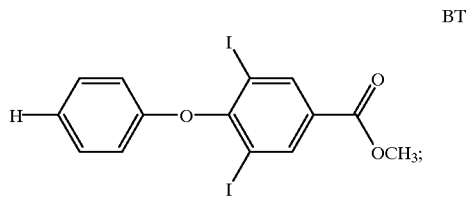

BTO-971
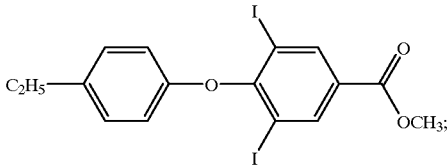

BTO-964
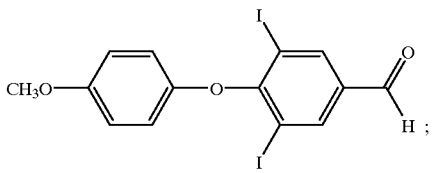

BTO-966
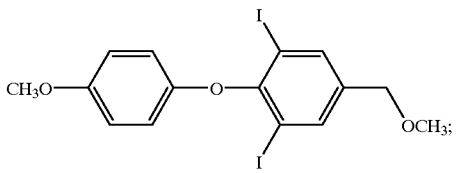

BTO-972
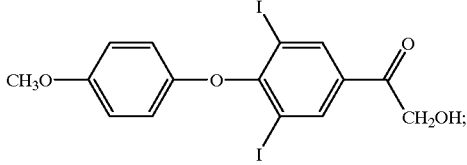

BTO-985
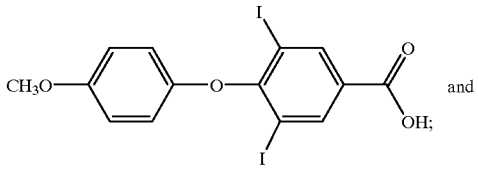

and

BTO-986
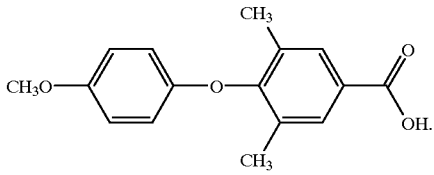

From the biological data provided herein, it is apparent that a number of substituents can be added to the aromatic rings of the compound of Formula I without affecting activity. Such substituents include, but are not limited to, alkyl, halogen, nitro and amino groups without any significant loss in biological activity. Moreover, although in preferred embodiments an ether oxygen connects the two aromatic rings, it should be understood that this group can be absent or, alternatively, replaced with a variety of groups or atoms that do not confine the aromatic rings to the same plane, such as, for example, a methylene group, a carboxy group or sulfur, without significant loss of biological activity. In addition, the chemical compounds referred to herein may exhibit the phenomena of tautomerism or conformational isomerism. As such, it should be understood that the invention encompasses any tautomeric or conformational isomeric forms which exhibit biological or pharmacological activities similar to those of the compounds described herein.

The compounds of the present invention can be synthesized in a variety of ways, using conventional synthetic chemistry techniques. Typically, the compounds of the present invention are prepared according to the reaction scheme set forth in FIG. 1, wherein A, Z, Y, X, $R^1$, $R^2$, $R^3$ $R^4$, $R^5$, $R^6$, $R^7$, $R^8$, $R^9$ and $R^{10}$ are as defined above. The use of appropriate organic solvents, temperature and time conditions for running the reactions are within the level of skill in the art. Suitable processes are illustrated by the representative examples. Necessary starting materials can be obtained by standard procedures of organic chemistry.

C. USES FOR THE COMPOUNDS OF THE PRESENT INVENTION

The compounds of the present invention can be used either in vivo or in vitro to inhibit the growth of a tumor cell. The compounds of the present invention are also useful because they bind tublin and exhibit antimitotic properties and, thus, can be used either in vivo or in vitro to inhibit abnormal cell mitosis. Moreover, the compounds of this invention can be used to inhibit the vascularization of endothelial cells and to inhibit angiogenesis. In addition, the compounds of this invention can be used to reduce the level of TNF-α produced by a cell. The compounds of the present invention are also useful in conjunction with other cancer therapies, including radiation therapy, chemotherapy and, in particular, immunotherapy (including radioimmunotherapy). Within this embodiment, the compounds of the present invention are particularly useful as sensitizing agents. When administered prior to, simultaneously with, or after treatment with a cancer therapy, the compounds of the invention increase the sensitivity of cancer cells to the therapy. This results not only in an increase in effectiveness of the therapy, but also can reduce the dosage required, thereby reducing undesirable side effects. It has been discovered that the compounds of the present invention are safe, effective, non-toxic and easy to administer.

As such, in one embodiment, the present invention provides a method of inhibiting the growth of a tumor cell, the method comprising contacting the tumor cell with a compound having the general formula:

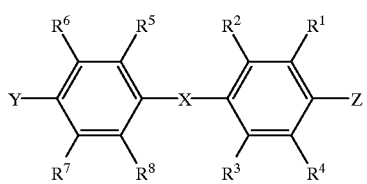

I or a pharmaceutically acceptable salt thereof.

In Formula I, $R^1$, $R^2$, $R^3$ and $R^4$ are each independently selected and are functional groups including, but not limited to, H, alkyl, S-alkyl, alkenyl, alkynyl, aryl, hydroxyl, alkoxy, halogen, $NO_2$ and $NH_2$. $R^5$, $R^6$, $R^7$ and $R^8$ are each independently selected and are functional groups including, but not limited to, H, alkyl, S-alkyl, alkenyl, alkynyl, aryl, hydroxyl, alkoxy and halogen.

In Formula I, X, if present, is a functional group including, but not limited to, the following:

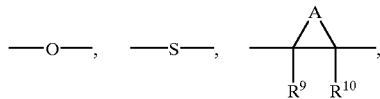

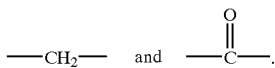

A, in the above formula, together with the carbons to which it is bound forms an optionally substituted 3, 4, 5 or 6 membered carbocyclic or heterocyclic ring. $R^9$ and $R^{10}$ in the above formula are independently hydrogen, alkyl and halogen. Y, in Formula I, is a functional group including, but not limited to, H, alkyl and alkoxy. Z is a functional group including, but not limited to, the following:

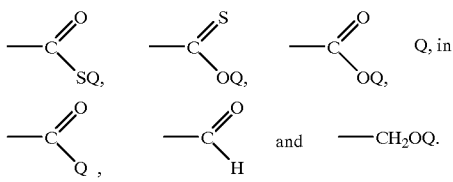

the above formula Z, is a functional group including, but not limited to, H, alkyl and S-alkyl.

With respect to the compound of Formula I, it should be noted that Z, Q and Y are selected such that if Z is

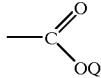

and Q is methyl, then Y is other than methoxy and ethoxy. Moreover, it should be noted that the prior discussions pertaining to X, Y, Z, $R^1$, $R^2$, $R^3$, $R^4$, $R^5$, $R^6$, $R^7$ and $R^8$ and their preferred embodiments are fully applicable to the compounds used in this method of the present invention and, thus, will not be repeated.

In accordance with the above method, tumor cells include, but are not limited to, lung, colon, breast, ovarian, prostate and hepatic tumor cells as well as squamous cell carcinomas. In a presently preferred embodiment, the tumor cells are present in a mammalian subject. Mammalian subjects include, but are not limited to, humans, laboratory animals, domestic pets and farm animals. In a further preferred embodiment, the above method further comprises the step of observing for a reduction in the growth of the tumor cells.

In another embodiment, the present invention provides a method of treating cancer, the method comprising administering to a mammalian subject having cancer a therapeutically effective amount of a compound having the general formula:

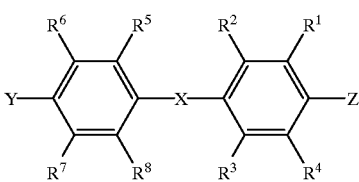

I or a pharmaceutically acceptable salt thereof. The prior discussions pertaining to A, X, Y, Z, $R^1$, $R^2$, $R^3$, $R^4$, $R^5$, $R^6$, $R^7$, $R^8$, $R^9$, and $R^{10}$ their definitions and preferred embodiments are fully applicable to the compounds used in the method to treat cancer and, thus, will not be repeated.

The compounds of the present invention are useful for treating a wide variety of cancers. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas. Moreover, in accordance with the above method, mammalian subjects include, but are not limited to, humans, laboratory animals, domestic pets and farm animals. In addition, it will be readily apparent to those of skill that using the compounds of Formula I, the growth of tumor cells can be inherited in other higher order organisms including, but not limited to, plants, insects, fish and the like.

Compounds suitable for use in the methods of the present invention can readily be identified using in vitro and in vivo screening assays. Such assays can screen for the ability of a particular compound to inhibit malignant tumor cell growth or to abolish tumorigenicity of malignant cells in vitro or in vivo. For instance, tumor cell lines can be exposed to varying concentrations of a compound of interest, and the viability of the cells can be measured at set time points using the alamar Blue® assay (commercially available from BioSource, International of Camarillo, Calif.). When alamar Blue dye is added to the culture medium, the dye is reduced by cellular mitochondrial enzymes yielding a soluble product with substantially enhanced fluorescence. This fluorescence can be measured with a fluorometer, whereby the signal is directly proportional to the cell number. Using this information, $IC_{50}$ (concentration of compound lethal to 50% of a cell culture as compared to a control culture) values for the compounds of interest can be readily be calculated. Generally, compounds useful in the methods of the present invention will exhibit an $IC_{50}$ in the range of about 0.1 to 20 $\mu M$, as measured by the assay described in Example IIA.

As will be appreciated by the skilled artisan, many varieties of malignant tumor cell cultures and cell lines can be used to screen for activity, including but not limited to MDA MB 231 (breast), MCF-7 (breast), MDA MB 468 (breast), Siha (squamous cell carcinoma), A549 (non-small cell lung), HL-60 (leukemia) Ovcar-3 (ovarian), etc. Of course, other in vitro and/or in vivo assays to screen for anti-tumor and/or anti-cancer activity known to and used by the skilled artisan can also be employed to identify effective compounds useful in the methods of the present invention.

In addition to the foregoing, the compounds of the present invention can be used to treat diseases characterized by abnormal cell mitosis. Such diseases include, but are not limited to, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

As such, in another embodiment, the present invention provides a method of treating a disease characterized by abnormal cell mitosis, the method comprising administering to a mammalian subject having such a disease a therapeutically effective amount of a compound having the general formula:

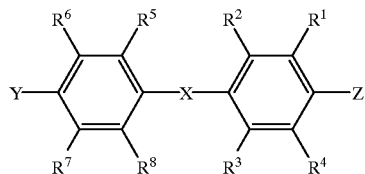

or a pharmaceutically acceptable salt thereof. The prior discussions pertaining to A, X, Y, Z, $R^1$, $R^2$, $R^3$, $R^4$, $R^5$, $R^6$, $R^7$, $R^8$, $R^9$ and $R^{10}$ their definitions and preferred embodiments are fully applicable to the compounds used in this method and, thus, will not be repeated.

Compounds suitable for use in the above method of the present invention can readily be identified using in vitro and in vivo screening assays. More particularly, a given compound can readily be screened for its anti-mitotic properties using, for example, the microtubule assembly inhibition assay and/or the competitive tubulin binding assay described in the examples. Other assays known to and used by those of skill in the art can also be used to screen a given compound for its anti-mitotic properties, or its anti-angiogenic properties by inhibition of growth of endothelial cells such as HUVEC (human umbilical vein endothelial cells) or HMVEC (human microvascular endothelial cells) in vitro or through the chicken chorioallantoic membrane (CAM) assay as discussed herein.

In another embodiment, the present invention provides methods of treating tumors in a mammal, by administering to the mammal an effective antineoplastic amount of ionizing or nonionizing radiation, or an effective antineoplastic amount of a chemotherapeutic agent, in conjunction with an effective sensitizing amount of a compound of Formula I. The compounds of the invention enhance the deleterious cellular effects caused by exposure to ionizing radiation or to a chemotherapeutic or immunotherapeutic agent. Such effects include, but are not limited to, damage to cellular DNA, such as DNA strand break, disruption in cellular function, such as by disrupting DNA function, cell death and the like. Often, a synergistic effect is observed when an effective sensitizing amount compound of Formula I is administered in conjunction with radiation therapy, chemotherapy, immunotherapy, or other cancer treatment. As used herein, a "synergistic effect" is achieved when a greater antineoplastic effect results with a conjunctive therapy than use of either drug or therapy alone. One advantage of conjunctive therapy with a synergistic effect is that lower dosages of one or both of the drugs or therapies may be used so that the therapeutic index is increased and toxic side effects are reduced.

Chemotherapeutic agents for which the compounds of Formula I are useful as sensitizers include, but are not limited to, alkylating agents, cross-lining agents, and DNA intercalating agents, interact covalently or non-covalently with cellular DNA causing certain deleterious cellular effects. For example, DNA-reactive agents include cisplatin, cyclophosphamide, diethylnitrosoamine, benzo(a)pyrene, carboplatin, doxorubicin, mitomycin-C and the like.

Techniques for determining an effective sensitizing amount of a compound of Formula I are known to those of skill in the art. In determining the effective sensitizing amount or dose, a number of factors are considered, including, but not limited to, the following: the species of mammal, its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

When used as a sensitizing agent, the compounds of Formula I can be administered as single doses or as multiple doses and are ordinarily administered prior to and/or during exposure to ionizing or nonionizing radiation or to chemotherapeutic agents. Generally, where a compound of the present invention is administered in conjunction with radiation therapy, the compound of the present invention will be administered in single or multiple doses prior to radiation therapy following a schedule calculated to provide the maximum selective sensitizing effect during radiation therapy. When a compound of the present invention is administered in conjunction with a chemotherapeutic agent, the compound of the present invention is generally administered in single or multiple doses prior to and during chemotherapy following a schedule calculated to provide the maximum selective sensitizing effect during chemotherapy.

In a particularly preferred embodiment, the compounds of Formula I are administered in combination with active immunotherapy (e.g., tumor vaccination). Because the compounds of Formula I are not immunotoxic, the immune system is not significantly suppressed and, thus, active immunotherapy can advantageously be carried out in combination with the chemotherapy. When used in conjunction with immunotherapy, the compound of Formula I can be administered prior to and/or during administration of the immunotherapeutic agent (e.g., a tumor vaccine).

The present invention also provides methods for preventing the development of a disease characterized by abnormal cell mitosis. Thus, the compounds of the present invention are useful not only for treating a tumor that already exists, but also for preventing the development of tumors or the reoccurrence of tumors. For example, one can administer a compound of Formula I to a mammal that is predisposed to the development of cancer, thereby reducing the likelihood that cancer will eventually occur. Alternatively, on can administer a compound of Formula I to a mammal that has previously had cancer, thereby reducing the likelihood that cancer will reoccur. For these applications, the compound is generally administered in multiple doses following a schedule calculated to reduce or eliminate abnormal cell proliferation. Appropriate dosage regimes can be determined by those of skill in the art using routinely practiced methods such as those discussed below.

In another embodiment this invention relates to a method of treating mammalian diseases associated with undesired and uncontrolled angiogenesis, the method comprising administering to a mammal an anti-angiogenic compound of Formula I in a dosage sufficient to inhibit angiogenesis. The particular dosage of a compound of Formula I required to inhibit angiogenesis and/or angiogenic diseases, according to this invention will depend upon the severity of the condition, the route of administration, and related factors that will be decided by the attending physician. Generally, accepted and effective daily doses will be the amount sufficient to effectively inhibit angiogenesis and/or angiogenic diseases.

In yet another aspect, this invention relates to a method of treating disease associated with angiogenesis. The methods of treatment provided by this invention are practiced by administering to a mammal in need thereof a dose of a compound of Formula I or a pharmaceutically acceptable salt or solvate thereof, that is effective to inhibit angiogenesis and/or angiogenic diseases. The term inhibit is defined to include its generally accepted meaning which includes prophylactically treating a human subject to incurring angiogenesis and/or angiogenic diseases, and holding in check and/or treating existing angiogenesis and/or angiogenic diseases. As such, the present method includes both medical therapeutic and/or prophylactic treatment, as appropriate.

The methods of the present invention can be used to treat a variety of diseases. Diseases associated with corneal neovascularization that can be treated according to the present invention include, but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease, periphigoid radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticurn, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue, including all forms of proliferative vitreoretinopathy, whether or not associated with diabetes.

Diseases associated with chronic inflammation can also be treated using the methods of the present invention. Diseases with symptoms of chronic inflammation include, but are not limited to, inflammatory bowel diseases, such as Crohn's disease and ulcerative colitis, psoriasis, sarcoidosis and rheumatoid arthritis. Unwanted or uncontrolled angiogenesis is a key element that these chronic inflammatory diseases all have in common. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the compositions and methods of the present invention prevent the formation of the granulomas, thereby alleviating the disease.

As mentioned above, the methods of the present invention can be used to treat patients with inflammatory bowel diseases, such as Crohn's disease and ulcerative colitis. Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

The inflammatory bowel diseases also exhibit extra intestinal manifestations, such as skin lesions. Such lesions are characterized by inflammation and angiogenesis and can occur at many sites other than in the gastrointestinal tract. The compositions and methods of the present invention can also be used to treat these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease can form anywhere in the body and, thus, the symptoms depend on the site of the granulomas and whether the disease active. The granulomas are created by the angiogenic capillary sprouts providing a constant supply of inflammatory cells. The compounds and method of this invention can be used to treat scaroidosis.

The methods of the present invention can also be used to treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated using the methods of the present invention is rheumatoid arthritis. Rheumatoid arthritis is a chronic inflammatory disease characterized by nonspecific inflammation of the peripheral joints. It is thought that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Other diseases that can be treated using the methods of the present invention are hemangiomas, Osler-Weber-Rendu disease, or hereditary hemorrhagic telangiectasia, solid or blood borne tumors and acquired immune deficiency syndrome.

Compounds suitable for use in the above methods of the present invention can readily be identified using in vitro and in vivo screening assays. Such assays may screen for the ability of a particular compound to inhibit angiogenesis or the vascularization of endothelial cells in vitro and in vivo. For instance, the chick embryo chorioallantoic membrane (CAM) assay, which is described in more detail below, can be used to screen a given compound for its ability to inhibit vascularization. In the chorioallantoic membrane assay, fertilized chick embryos are removed from their shell on day 3 or 4, and a methylcellulose disc containing a compound of Formula I is implanted on the chorioallantoic membrane. The embryos are examined 48 hours later and, if a clear avascular zone appears around the methylcellulose disc, the diameter of that zone is measured. This assay can be used to assess the anti-angeogenic properties of the compounds of Formula I.

Another useful screening assay to assess the efficacy of compounds of Formula I is the corneal micropocket angiogenesis assay (CMA). The rat corneal micropocket assay can be used to assess the ability of the compounds of Formula I to inhibit corneal angiogenesis (see, "Quantitative Angiogenesis Assays: Progress and Problems," *Nat. Med.,* 3: 1203–1208 (1997) and "Inhibition of Tumor Angiogenesis Using a Soluble Receptor Establishes a Role for Tie2 in Pathologic Vascular Growth." *J. Clin. Invest.,* 100: 2072–2078. (1997).) In this assay, the compound of Formula I is mixed with a polymer (e.g., Hydron solution; Interferon Sciences, New Brunswick, N.J.) and implanted in a small-pocket surgically created in the superficial layers of the cornea of a rat. Under normal circumstances, this wound stimulates an angiogenic response which is readily visible as the appearance of neovessels on the normally avascular cornea. If the compound of Formula I is effective, specifically as an anti-angiogenic agent, it inhibits or blocks this response. In one experimental design, a group of five animals (including a control group with only polymer implants) is tested over a range of drug doses which can induce tumor growth delay. Three doses are tested in the assay. Assessment of an anti-angiogenic response by this method is categorical. In other words, a treated eye is either positive or negative for corneal angiogenesis. This assay determines whether a compound of Formula I is directly anti-angiogenic in an in vivo mammalian model of angiogenesis.

In addition, the human microvascular endothelial cell assay (HMVEC) can be used to assess the efficacy of compounds of Formula I. HMVEC are seeded into a 96-well plate at a concentration of $5 \times 10^3$ cells/well in a volume of 100 $\mu$l/well of Endothelial Growth Medium. Plates are then incubated at 37° C. in 5% $CO_2$ for 24 h and then aliquots of the compound of Formula I are added to the HMVEC preparations and plates are then incubated at 37° C. in 5% $CO_2$ for 3 days. The relative number of cells is determined by adding 20 $\mu$l/ml of Alamar Blue for 3–6 h at 37° C. and measuring color changes indicating metabolic activity by using a Fluorescence Measurement System. In this assay, the intensity of the fluorophore signal is directly proportional to cell number.

The HMVEC assay can also be carried out using human umbilical vein microvascular endothelial cells (HUMVEC). The assay is carried out similarly to the above assay, but HUMVEC cells are used.

In still another embodiment, the present invention provides a method for reducing the level of TNF-α produced by a cell. TNF-α and its various modes of action are generally described by Abbas, et al., *Cellular and Molecular Immunology,* Abbas, et al., 2nd Ed., W. B. Saunders Company, 1994, pp. 244–249, the teachings of which are incorporated herein by reference. TNF-α plays an integral role in destroying tumors, mediating responses to tissue injury and protecting hosts from infections by various microorganisms. However, its activity appears to be excessive in some disease states and inflammatory reactions such as rheumatoid arthritis, cachexia and septic shock. The excess TNF-α results in an exaggerated immune response exemplified by over stimulation of interleukin-6 and granulocyte/macrophage-colony stimulating factor (GM-CSF) secretion, enhanced cytotoxicity of polymorphonuclear neutrophils and prolonged expression of cellular adhesion molecules, all of which can have detrimental effects.

Contacting cells with the compounds of Formula I results in decreased levels of TNF-α. Without intending to be bound by any theory, reduced levels of TNF-α can result from any of several possible mechanisms including, but not limited to, downregulation of expression of a gene that encodes TNF-α, a reduction in TNF-α mRNA stability or translation efficiency, decreased stability of the TNF-α polypeptide, and reduced secretion of TNF-α from a cell. Reduced levels of TNF-α can be measured in a cell, biological sample or the blood stream. As a result of their ability to inhibit TNF-α, the compounds of Formula I can be used to treat inflammatory diseases. Such diseases include, but are not limited to, the inflammatory diseases set forth above (e.g., chronic inflammation, chronic disease, inflammatory bowel disease, sarcoidosis, psoriasis, rheumatoid arthritis, and the like). Using the assay set forth in Example VIII, compounds of Formula I can readily be screened for their ability to reduce TNFα.

TNF-α is noted for its pro-inflammatory actions which result in tissue injury, such as induction of procoagulant activity on vascular endothelial cells, increased adherence of neutrophils and lymphocytes and stimulation of the release of platelet activating factor from macrophages, neutrophils and vascular endothelial cells. As such, targeting moieties which are directed to these cells and which are conjugated to liposomes or other drug delivery systems comprising the compounds of Formula I are preferred embodiments of this invention. For instance, in a preferred embodiment, monoclonal antibodies to TNF-α (Tracey, et al., *Nature* 1987, 330, 662–664; Silva, et al., *J. Infect. Sis.* 1990, 162, 421–427; and Williams, et al., *Proc. Natl. Acad. Sci.* 1992, 89, 9784–9788) are conjugated to liposomes comprising compounds of Formula I.

Moreover, in accordance with the above methods, mammalian subjects include, but are not limited to, humans, laboratory animals, domestic pets and farm animals.

D. PHARMACEUTICAL FORMULATIONS/ROUTES OF ADMINISTRATION

The compounds of the present invention can be administered to a mammal, e.g., a human patient, alone, in the form of a pharmaceutically acceptable salt, or in the form of a pharmaceutical composition where the compound is mixed with suitable carriers or excipient(s) in a therapeutically effective amount, e.g., at doses effective to depress or suppress malignant cell growth or result in amelioration of symptoms associated with cancerous diseases.

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Moreover, the compound can be administered in a local rather than systemic manner, for example via injection of the compound directly into a solid tumor, often in a depot or sustained release formulation. In addition, the compounds can be administered in a targeted drug delivery system, for example, in a liposome coated with tumor-specific antibody. Such liposomes will be targeted to and taken up selectively by the tumor.

The compounds of the present invention can be administered alone, in combination with each other, or they can be used in combination with other known compounds (e.g., other anti-cancer drugs or other drugs, such as AZT, anti-inflammatories, antibiotics, corticosteroids, vitamins, etc.). More particularly, the compound of the present invention can be used in conjunctive therapy with other known chemotherapeutic or antineoplastic agents (e.g., vinca alkaloids, antibiotics, antimetabolites, platinum coordination complexes, etc.). For instance, the compounds of the present invention can be used in conductive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; or a platinum coordination complex, such as cisplatin (cis-DDP), carboplatin, etc. In addition, those of skill in the art will appreciate that the compounds of the present invention can be used in conjunctive therapy with other known chemotherapeutic or antineoplastic compounds. In pharmaceutical dosage forms, the compounds may be administered in the form of their pharmaceutically acceptable salts, or they may also be used alone or in appropriate association, as well as in combination with other pharmaceutically active compounds.

Suitable formulations for use in the present invention are found in *Remington's Pharmaceutical Sciences* (Mack Publishing Company, Philadelphia, Pa., 17th ed. (1985)), which is incorporated herein by reference. Moreover, for a brief review of methods for drug delivery, see, Langer, *Science* 249:1527–1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

In addition, in a presently preferred embodiment, the compounds of Formula I can be administered in a targeted drug delivery system, for example, in a liposome coated with a tumor-specific antibody. Such liposomes will be targeted to and taken up selectively by the site of interest (e.g., tumor cell). Liposomes and emulsions are well known examples of delivery vehicles or carriers for hydrophobic drugs. In a presently preferred embodiment, long-circulating, i.e., stealth, liposomes are employed. Such liposomes are generally described in Woodle, et al., U.S. Pat. No. 5,013,556, the teachings of which are hereby incorporated by reference.

Generally, such liposomes or other drug delivery systems typically have a targeting moiety, i.e., ligand, conjugated thereto that is specific for the target site of interest (e.g., tumor cell). For instance, some property (biochemical, architectural, or genetic) of the tumor that is different from normal tissue can be exploited to concentrate the compounds of Formula I in, or at least near, the target tumor. Tumor vasculature, which is composed primarily of endothelial cells, is inherently different than normal differentiated vasculature. For example, the architecture of tumor vasculature is different, i.e., the vessels are known to be leaky, and blood flow through them is mostly intermittent, with periods of perfusion and periods of occlusion and subsequent hypoxia. This aberrant microenvironment may be caused by and, in turn, leads to additional, differential gene expression in tumor vasculature relative to normal vasculature. This abnormal architecture and function, at the molecular level, is characterized by differences in surface markers in tumor microvessels relative to normal vessels and such differences can be exploited to target the liposome or other drug delivery system to the site of interest.

Monoclonal antibodies directed against a tumor marker TNF-α, TNF-α receptor, vasculatures of endothelial cells, etc. is one strategy that can be employed. Other strategies which can be employed is the targeting of a marker on abnormal tumor vasculature. The targeting moiety when coupled to a liposome or other drug delivery system containing a drug or radioisotope win act to concentrate the drug where it is needed. Ligands for tumor-associated vessel markers can also be used. For example, a cell adhesion molecule that binds to a tumor vascular element surface marker can be employed. Liposomes and other drug delivery systems can also be used, especially if their surface contains a ligand to direct the carrier preferentially to the tumor vasculature. Liposomes offer the added advantage of shielding the drug from most normal tissues, thereby reducing the inherent toxicity of many compounds. When coated with polyethylene glycol (PEG) (i.e., stealth liposomes) to minimize uptake by phagocytes and with a tumor vasculature-specific targeting moiety, liposomes offer longer plasma half-lives, lower non-target tissue toxicity, and increased efficacy over non-targeted drug.

Other targeting strategies include, but are not limited to, ADEPT (antibody-directed enzyme prodrug therapy), GDEPT (gene-directed EPT) and VDEPT (virus-directed EPT). In ADEPT, the targeting of an inactive prodrug to a tumor mass is effected by an antibody against a tumor-associated marker. The enzyme milieu in or about the tumor transforms the prodrug into an active toxic agent that then acts on the tumor tissue. Similarly, differential gene expression or viral targeting at the tumor site is used to activate a prodrug into its active, toxic form in GDEPT and VDEPT, respectively. Other strategies include targeting differentially expressed genes, enzymes or surface markers that appear on, for example, tumor-associated vasculature to effect control of tumor growth. Using the foregoing methods, the compounds of Formula I can be targeted to the tumor vasculature to effect control of tumor progression or to other sites of interest (e.g., endothelial cells, TNF-α, TNF-α receptor, etc.).

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the invention, a therapeutically effective dose can be estimated initially from cell culture assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans. Initial dosages can also be estimated from in vivo data.

Initial dosages can also be formulated by comparing the effectiveness of the compounds described herein in cell culture assays with the effectiveness of known anticancer drugs such as vincristine. In this method an initial dosage can be obtained by multiplying the ratio of effective concentrations obtained in cell culture assay for the a compound of the present invention and a known anti-cancer drug by the effective dosage of the known anti-cancer drug. For example, if a compound of the present invention is twice as effective in cell culture assay than vincristine (i.e., the $IC_{50}$ of that compound is equal to one-half the $IC_{50}$ of vinicristine in the same assay), an initial effective dosage of the compound of the present invention would be one-half the known dosage for vincristine. Using these initial guidelines one having ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1).

Dosage amount and interval may be adjusted individually to provide plasma levels of the active compound which are sufficient to maintain therapeutic effect. Usual patient dosages for oral administration range from about 50–2000 mg/kg/day, commonly from about 100–1000 mg/kg/day, preferably from about 150–700 mg/kg/day and most preferably from about 250–500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

I. THE COMPOUNDS

A. Synthesis of methyl 3,5-diodo-4-(4-methoxyphenoxy)benzoate: BTO-956

The synthesis of BTO-956 is accomplished in a series of steps, first yielding methyl 3,5-dinitro-4-(4-methoxyphenoxy)benzoate, the nitro groups of which are then reduced to amines and subsequently replaced by iodine. The method for preparing BTO-956 is essentially as described in: Masuda, K., Imashiro, Y., and Okada, Y. Synthesis of triiodothyroformic acid and its derivatives. *J. Takeda Res. Lab.* 1970, 29, 545–552. The synthesis of the ethyl analog, BTO-957, is an adaptation of this same procedure.

1. Methyl 3,5-dinitro4-(4-methoxyphenoxy)benzoate

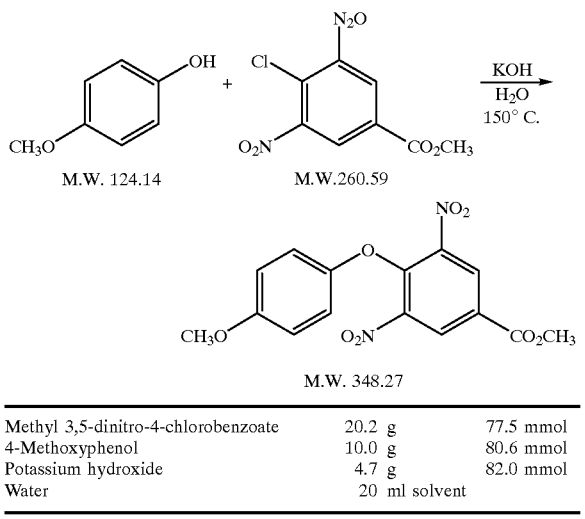

| | | |
|---|---|---|
| Methyl 3,5-dinitro-4-chlorobenzoate | 20.2 g | 77.5 mmol |
| 4-Methoxyphenol | 10.0 g | 80.6 mmol |
| Potassium hydroxide | 4.7 g | 82.0 mmol |
| Water | 20 ml solvent | |

To a 100 ml round-bottomed flask containing potassium hydroxide (4.7 g; 82.0 mmol) dissolved in water (20 ml) was successively added 4-methoxyphenol (10.0 g; 80.6 mmol) and methyl 4-chloro-3,5-dinitrobenzoate (20.2 g; 77.5 mmol). The flask was fitted with a reflux condenser and the reaction heated at 150° C. (oil bath) for 3 hours. After cooling to room temp, the reaction mixture was transferred to a large mortar and triturated with cold 2N NaOH (100 ml) to remove unreacted phenol. The solid was collected by filtration and air-dried to give 21.5 g of crude product. Crystallization from absolute ethanol gave 17.7 g (65.6%) of pure methyl 3,5-dinitro-4-(4-methoxyphenoxy)benzoate as light yellow needles. 300 MHz $^1$H NMR (CDCl$_3$) d 3.77 (s, 3H, OCH$_3$), 4.02 (s, 3H, OCH$_3$), 6.82 (m, 4H, ArH), 8.70 (s, 2H, ArH).

2. Methyl 3, 5-diamino4-(4-methoxyphenoxy)benzoate

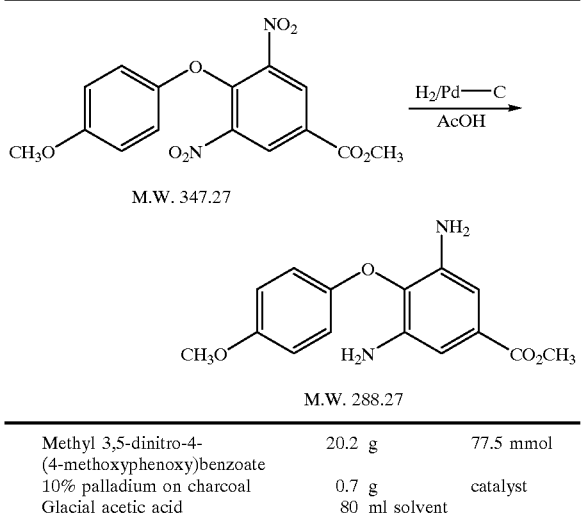

| | | |
|---|---|---|
| Methyl 3,5-dinitro-4-(4-methoxyphenoxy)benzoate | 20.2 g | 77.5 mmol |
| 10% palladium on charcoal | 0.7 g | catalyst |
| Glacial acetic acid | 80 ml solvent | |

To a Parr shaker bottle containing a suspension of methyl 3,5-dinitro-4-(4-methoxyphenoxy)-benzoate (20.2 g; 77.5 mmol) in glacial acetic acid (80 ml) was added 10% palladium on charcoal (0.7 g). The bottle was shaken under an atmosphere of hydrogen (3 atm) until no more hydrogen was consumed. The catalyst was filtered off and the resulting solution concentrated to approximately 10 ml. The residue was dissolved in acetone (50 ml) and heated on a steam bath while water (100 ml) was added in portions. Upon cooling, medium brown needles formed which were collected by suction filtration and dried to give 7.1 g (86%) of methyl 3,5-diamino-4-(4-methoxyphenoxy)benzoate. 300 MHz $^1$H NMR (CDCl$_3$) d 3.73 (s, 3H, OCH$_3$), 3.80 (bs, 4H, ArNH$_2$) 3.86 (s, 3H, OCH$_3$), 6.84 (m, 4H, ArH), 6.91 (s, 2H, ArH).

3. Methyl 3,5 -diiodo-4-(4-methoxyphenoxy)benzoate (BTO-956)

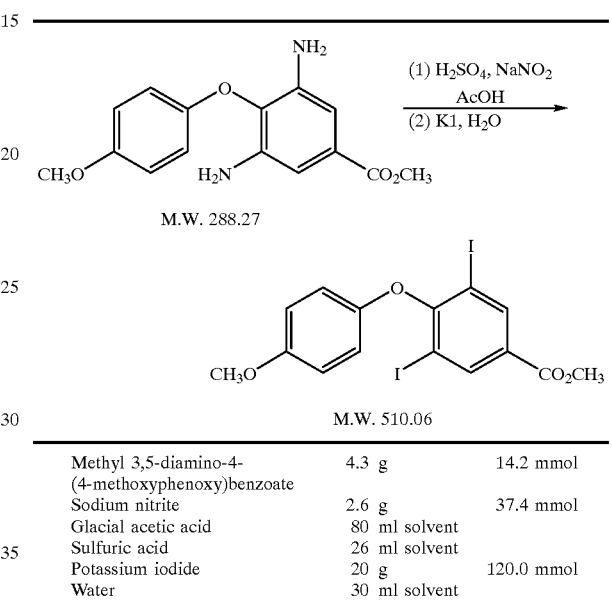

| | | |
|---|---|---|
| Methyl 3,5-diamino-4-(4-methoxyphenoxy)benzoate | 4.3 g | 14.2 mmol |
| Sodium nitrite | 2.6 g | 37.4 mmol |
| Glacial acetic acid | 80 ml solvent | |
| Sulfuric acid | 26 ml solvent | |
| Potassium iodide | 20 g | 120.0 mmol |
| Water | 30 ml solvent | |

Sulfuric acid (26 ml) was placed in a three-necked flask equipped with a mechanical stirrer and cooled in an ice bath. Sodium nitrite (2.58 g, 37.4 mmol) was added in small portions, and the mixture was stirred for 20 min to form a thick solution. To this was added a slurry of methyl 3,5-diamino-4-(4-methoxyphenoxy)benzoate (4.30 g, 14.22 mmol) in glacial acetic acid (80 ml), dropwise over a period of 30 min, keeping the temperature below 10° C. with the ice bath. The reddish brown solution was stirred at below 10° C. for 45 min, after which it was poured slowly into an aqueous (30 ml) solution of potassium iodide (20 g) at RT, with vigorous stirring. A thick suspension formed, and was allowed to stir at RT for 1 h. The reaction mixture was then heated in an oil-bath to 80° C. (internal temperature) for 15 min, and then allowed to cool to RT. The solution was filtered and the black gummy residue was dissolved in 300 ml of acetone. The dark filtrate, when refrigerated overnight, deposited a dark residue, which was collected by decanting the supernatant, and the residue was dissolved in 100 ml of acetone. The combined acetone solution was filtered over a pad of basic alumina (5 cm) in a 150 ml sintered glass funnel to remove some colored impurities. The alumina pad was washed with 100 ml acetone and the red filtrate was evaporated to dryness, to give a dark solid as crude product. This was purified by flash chromatography on silica gel, eluting with hexanes-CH$_2$Cl$_2$ (60:40). Initial fractions containing the pure product were pooled and evaporated to yield 1.67 g of the desired product as an off-white solid. This compound gave a single, clean spot on TLC (Hexanes: CH$_2$Cl$_2$;

1:1; $R_f$ 0.35). Impure fractions were pooled and triturated with absolute EtOH for 16 hours at RT. The solid was filtered and dried to yield another 0.3 g of the product as a cream solid, which contained ~5% of the slow-moving impurity as evidenced by TLC ($R_f$ 0.29). Total yield of the product was 27%. 300 MHz $^1$H NMR (CDCl$_3$) d 3.78 (s, 3H, OCH$_3$), 3.94 (s, 3H, COOCH$_3$), 6.70 and 6.83 (two d, AA'XX', 4H, p-subs. Ar-H), 8.51 (s, 2H, Ar—H).

B. Synthesis of methyl 3,5-diiodo-4-(4-ethoxyphenoxy)benzoate: BTO-957

The synthesis of BTO-957 is achieved by essentially the same method used to produce BTO-956, as described above (structures not shown), with the most notable exception being the use of 4-ethoxyphenol as a starting reagent instead of 4-methoxyphenol. The stepwise synthesis yields first methyl 3,5-dinitro-4-(4-ethoxy-phenoxy) benzoate, the nitro groups of which are then reduced to amines and subsequently replaced by iodine.

1. Methyl 3,5-dinitro4-(4-ethoxyphenoxy)benzoate

A mixture of 13 g (50 mmole) of methyl 4-chloro-3,5-dinitrobenzoate, 7.45 g (54 mmole) of 4-ethoxyphenol, and 13 ml of potassium hydroxide solution (3.03 g, 54 mmole) was heated under argon at 150° C. for 4 h. The mixture was cooled and partitioned between 130 ml of 2 N sodium hydroxide solution and 400 ml of dichloromethane. The organic layer was washed with 2×100 ml of saturated sodium bicarbonate solution, dried over magnesium sulfate and evaporated under high vacuum to give 14.5 g, which was chromatographed on a silica gel column (5 cm×50 cm), eluting with 25% hexane/75% dichloromethane to give 13.2 g (74% yield). TLC (silica gel, CH$_2$Cl$_2$), $R_f$ 0.80. NMR: $^1$H (300 MHz) (CDCl$_3$) 1.39 (3H, t, —CH$_3$); 3.97 (2H, q, —CH$_2$—); 4.02 (3H, s, —OCH$_3$); 6.81 (4H, s, arom); and 8.70 ppm (2H, s, arom).

2. Methyl 3,5-diamino-4-(4-ethoxyphenoxy)benzoate

A solution of 24 g (66.2 mmole) of methyl 3,5-dinitro-4-(4-ethoxy-phenoxy) benzoate in 200 ml of glacial acetic acid was hydrogenated with 2.0 g of 10% palladium on carbon at 50 mm Hg over 30 min. The catalyst was removed by filtration through celite. The filter cake was washed with 20 ml of acetic acid and the combined organic solution was poured into 2 L of water. A white precipitate immediately formed which was filtered and dried overnight under high vacuum to give 16.31 g (82%). TLC (silica gel, CH$_2$Cl$_2$), $R_f$ 0.2–0.4 (streak). NMR: $^1$H (300 MHz) (CDCl$_3$) 1.38 (3H, t, —CH$_3$); 3.87 (3H, s, —OCH$_3$); 3.98 (2H, q, —CH$_2$—); 6.82 (4H, m, arom); and 6.93 ppm (2H, s, arom).

3. Methyl 3,5-diiodo4-(4-ethoxyphenoxy)benzoate (bto-957)

To 60 ml of concentrated sulfuric acid in a 250 ml three necked flask equipped with an overhead stirring motor and cooled to 0° C. in an ice bath was added 6.20 g (90 mmole) of sodium nitrite in portions over 20 min, keeping the temperature of the reaction mixture below 10° C. To this solution was added a solution of 10.8 g (35.9 mmole) of methyl 3,5-diamino-4-(4-ethoxyphenoxy)benzoate in 50 ml of glacial acetic acid dropwise over 45 min while keeping the temperature of the reaction below 10 ° C. The reaction was stirred at 0° C. for an additional 30 min and poured into 50 g (300 mole) of potassium iodide in 100 ml of water. This solution was allowed to stand for 1 h. The mixture was heated to 80° C. over 5 min on a steam bath and cooled to room temperature. To this solution was added 1 L of water and a gummy precipitate was collected. The precipitate was dissolved in 400 ml of acetone and filtered through a 5 cm X 10 cm column of basic alumina. The eluate was evaporated to give a red gum which was chromatographed on a 5 cm X 50 cm silica gel column, eluting with 50% hexane/ 50% dichloromethane The product was collected to give 8.5 g of a white solid. This solid was triturated with 80 ml of 95% ethanol to give 8.4 g of a white solid (36% yield). MS (EI) m/e 524 (M$^+$, 100%). TLC (50% hexane/50% CH$_2$Cl$_2$), $R_f$ 0.50. NMR: $^1$H (300 MHz) (CDCl$_3$) 1.39 (3H, t, —CH$_3$); 3.93 (3H, s, —OCH$_3$); 3.99 (2H, q, —CH$_2$—); 6.75 (4H, q, arom); and 8.51 ppm (2H, s, arom).

C. Synthesis of Methyl 3,5-diodo-4-(4'-methoxyphenoxy)thiobenzoate (BTO-967)

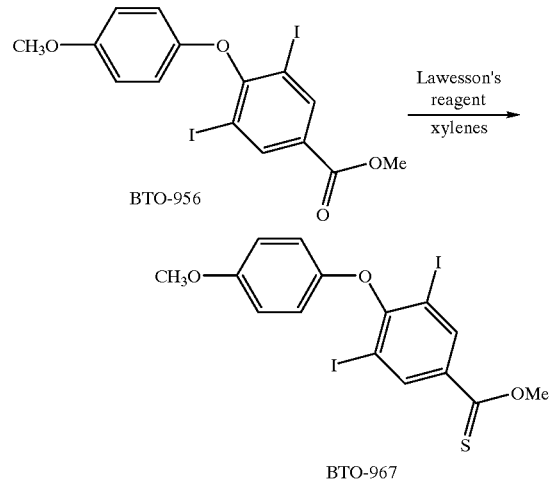

To a solution of methyl 3,5-diiodo-4-(4'-methoxyphenoxy)benzoate [BTO-956] (5.10 g; 10.0 mmol) in dry xylene (10 ml) was added Lawesson's reagent [2,4-bis(methoxyphenyl)-1,3-dithia-2,4-diphosphetane-2,4-disulfide](4.85 g; 12.0 mmol) and the reaction stirred at reflux for 24 h. The cooled mixture was evaporated to an orange residue, applied to a pad of silica gel (20 g), and eluted with CH$_2$Cl$_2$/petroleum ether (1:1). Product-containing fractions were pooled and concentrated under reduced pressure to give an orange oil. The material was further purified on a silica gel column (26 cm X 2 cm) by eluting the compound with CH$_2$Cl$_2$/petroleum ether (1:4). The product began to crystallize spontaneously upon elution. The material was allowed to crystallize overnight, and was then collected by using suction filtration and air-dried to give 1.36 g (26%) of methyl 3,5-diiodo-4-(4'-methoxyphenoxy)thiobenzoate (1) as a yellow crystalline solid. NMR (CDCl$_3$) d 3.78 (s, 3H), 4.29 (s, 3H), 6.72 (m, 2H), 6.83 (m, 2H), 8.66 (s, 2H).

D. Synthesis of 3,5-Diiodo-4-(4'-methoxyphenoxy) benyl alcohol (BTO-972).

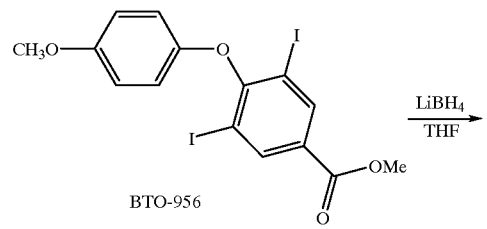

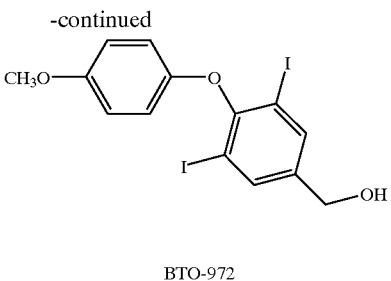

BTO-972

To a dry 15 ml 2-necked flask fitted with a serum stopper and a reflux condenser under argon was added methyl 3,5-diiodo-4-(4'-methoxyphenoxy)benzoate (1.02 g; 2.0 mmol) followed by 2M LiBH$_4$ in THF (2.0 ml; 4.0 mmol). The mixture was stirred at RT overnight. EtOAc (10 ml) was added to consume excess LiBH$_4$, and the resulting mixture stirred at RT under argon. After approximately 20 min, a moderate exotherm was observed and the reaction became cloudy. The reaction was digested with saturated NH$_4$Cl (20 ml), EtOAc added (20 ml) and the resulting layers partitioned and separated. The organic layer was washed with saturated NaCl (25 ml), then dried over Na$_2$SO$_4$, filtered and evaporated to give a pale amber oil. The crude product was applied to a filter pad of silica gel (10 g, 230–400 mesh) and eluted with EtOAc/hexanes (3:7). Fractions containing product were combined and evaporated to give 592 mg (61%) of the product as a white solid. Crystallization from EtOAc/hexanes afforded 347 mg of 3,5-diiodo-4-(4'-methoxyphenoxy)benzyl alcohol (9) as a crystalline white solid. NMR (CDCl$_3$) d 3.78 (s, 3H), 4.52 (s, 2H), 6.72 (m, 2H), 6.83 (m, 2H), 7.82 (s, 2H). TLC: R$_f$0.47 (EtOAc/hexanes, 3:7)

E. Synthesis of 3,5-Diiodo-4-(4'-methoxyphenoxy)benzadehyde (BTO-964)

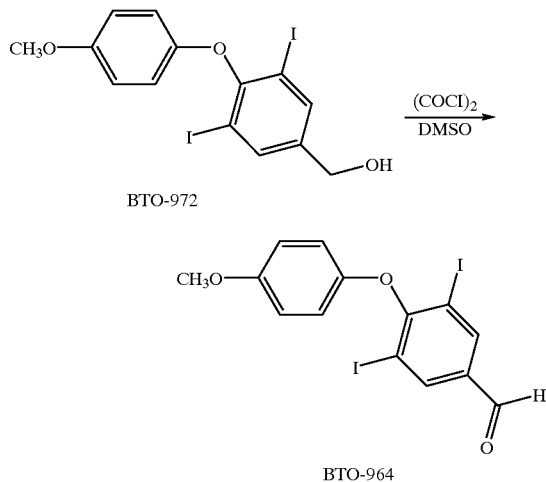

To a solution of 2M oxalyl chloride in CH$_2$Cl$_2$ (0.57 ml; 1.1 mmol) was added dry CH$_2$Cl$_2$ (2.5 ml) under argon. The solution was cooled to −55° C. (dry ice/acetone) and DMSO (178 ml, 2.5 mmol) in CH$_2$Cl$_2$ (400 ml) was added slowly over 1 min. After 3 min, a solution of 3,5-diiodo-4-(4'-methoxyphenoxy)benzyl alcohol (9) (432 mg; 0.9 mmol) in CH$_2$Cl$_2$ (800 ml) was added in one portion. After stirring the mixture for 15 min, triethylamine (733 ml; 5.2 mmol) was added and the reaction was stirred an additional 5 min at −55° C. before being allowed to warm to RT. The reaction was quenched with water (10 ml) and then diluted with EtOAc (10 ml). The organic layer was separated, washed sequentially with dilute HCl, saturated NaHCO$_3$, and saturated NaCl, then dried over Na$_2$SO$_4$, filtered and evaporated to a tan solid. The crude product was applied to a filter pad of silica gel (10 g, 230–400 mesh) and eluted with EtOAc/hexanes (3:7). Fractions containing product were combined and evaporated to give 360 mg (84%) of the product as a pale yellow solid. Crystallization from EtOAc/hexanes gave 175 mg (41%) of methyl 3,5-diiodo-4-(4'-methoxyphenoxy)-benzaldehyde (8) as an off-white crystalline solid. NMR (CDCl$_3$) d 3.78 (s, 3H), 6.73 (m, 2H), 6.84 (m, 2H), 8.34 (s, 2H), 9.87 (s, 1H). TLC: R$_f$0.67 (EtOAc/hexanes, 3:7)

F. Synthesis of 3,5-Diiodo-4-(4'-methoxyphenoxy)benzyl methyl ether (BTO-966)

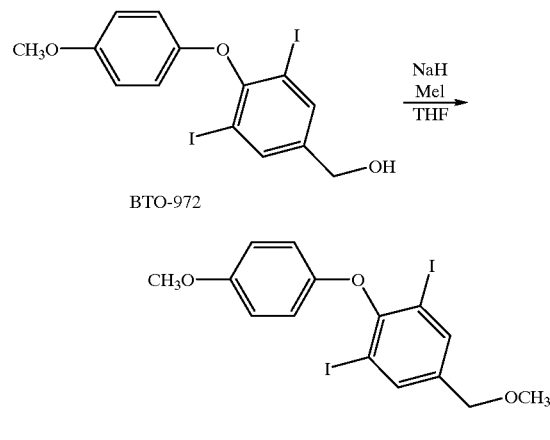

A solution of 3,5-diiodo-4-(4'-methoxyphenoxy)benzyl alcohol (9) (347 mg; 0.72 mmol) in dry THF under argon was cooled to 0° C. and treated with 60% sodium hydride in mineral oil (28 mg; 0.7 mmol). The reaction was stirred at 0° C. for 10 min, then allowed to warm to RT and stirred an additional 30 min. Methyl iodide (0.5 ml; 8.1 mmol) was added and the mixture stirred at RT for 18 h. The reaction was poured into saturated NH$_4$Cl (20 ml) and extracted with EtOAc (20 ml). The organic layer was washed with saturated NaCl, dried over Drierite, and evaporated to a tan oil which solidified upon standing. The solid was dissolved in a minimum amount of CH$_2$Cl$_2$ (3 ml), applied to a silica gel column (30 g, 230–400 mesh) and eluted with EtOAc/hexanes (3:17). Product-containing fractions were combined and evaporated to give 231 mg of 3,5-diiodo-4-(4'-methoxyphenoxy)benzyl methyl ether (10) as a white solid. NMR (CDCl$_3$) d 3.41 (s, 3H), 3.76 (s, 3H), 6.70 (m, 2H), 6.81 (m, 2H), 7.80 (s, 2H). TLC: R$_f$0.69 (EtOAc/hexanes, 3:7)

II. ANTITUMOR EFFICACY OF BTO-956, 964, 966 AND 967

A. In vitro cytotoxicity screen against human tumor cell lines.

Human tumor cell lines were exposed continuously to varying concentrations of test agents, i.e., BTO-956, BTO-964, BTO966 and BTO-967) and the viability of the cells was measured at set time points (1, 3, and 7 days) using the alamar Blue™ assay. When alamar Blue dye is added to culture medium, the dye is reduced by cellular mitochondrial enzymes yielding a soluble product with substantially enhanced fluorescence. This fluorescence can be measured with a fluorimeter, whereby the signal is directly proportional to cell number.

Various tumor cell lines of human origin representing a wide diversity of cancer pheno- and genotypes were exposed in vitro to the agents to evaluate the drug's effective range. Tumor lines screened included MDA MB 231 (breast), MCF-7 (breast), MDA MB 468 (breast), Siha (squamous cell carcinoma), A549 (non-small cell lung), HL-60 (leukemia), Ovcar-3 (ovarian). The test agents were prepared in serial dilutions from 10 mM stock solutions in DMSO yielding a 66-fold dose range of 20 $\mu$M, 10 $\mu$M, 3 $\mu$M, 1 $\mu$M and 0.3 $\mu$M concentrations. In each case, cells were maintained at 37° C. under 5 percent $CO_2$ in air. All cell lines were incubated in Dulbecco's modified Eagle medium (DMEM) supplemented with 10% heat-inactivated fetal bovine serum and graded doses of BTO-956, 964, 966, or 967. 5-Fluorouracil (5-FU) was included as a positive control in experiments with two of the cell lines. The experiments were conducted in 96-well tissue culture plates (Falcon) with an initial seeding density of 1000 cells per well in 250 $\mu$l aliquots. The next day, medium was replaced with 100 $\mu$l of drug dilutions in triplicate.

After a 7 day exposure to the various agents, the alamar-Blue dye was diluted to 20% in DMEM, and 100 $\mu$l was added to each well. The cells were incubated for 8 hours until obvious color changes indicated sufficient amounts of reduced dye for quantitation. Relative cell number was evaluated by florimetry on a Millipore 2300 CytoFluor fluorescence measurement system. Measurements were taken directly from 96-well plates after excitation at 560 nm with concomitant emission at 590 nm. $IC_{50}$ values were calculated vs. control (nontreated cells); results are presented in Table 1.

TABLE 1

Cytotoxicity of Representative Lead Compounds Against Human Cancer Cell Lines[a]

| Cell line | $IC_{50}$ ($\mu$M) BTO-956 | $IC_{50}$ ($\mu$M) BTO-964 | $IC_{50}$ ($\mu$M) BTO-966 | $IC_{50}$ ($\mu$M) BTO-967 | $IC_{50}$ ($\mu$M) 5-FU |
|---|---|---|---|---|---|
| A549 | 4.0 | >20 | >30 | 5.5 | 5.5 |
| OVCAR 3 | <0.3 | 1.8 | 6.9 | 0.8 | ND[b] |
| MDA MB 231 | 10 | 2.0 | 10 | 2.0 | 10 |
| MDA MB 468 | 0.5 | 4.0 | 7.5 | 1.5 | ND[b] |
| MCF 7 | 5.0 | 2.4 | 7.0 | 1.0 | ND[b] |
| Siha | 0.5 | 17 | >20 | 20 | ND[b] |

[a]Cytotoxicity determined 7 days post exposure
[b]Not determined

B. In vitro metabolism of BTO-956, 964, 966, and 967 in human leukemia cells

In humans and laboratory animals, enzyme systems in the liver are capable of metabolizing a large number of chemicals to inactive forms, and some chemotherapeutic agents are inactive unless they are metabolized to active forms. To test for either of these possibilities, the compounds, i.e., BTO-956, BTO-964, BTO-966 and BTO-967, were incubated with a microsomal enzyme fraction, referred to as S9. Human leukemia (HL60) cells were used to evaluate drug metabolism. Exposure to the test article was performed in the presence and absence of S9, prepared from the liver of adult male rats given a single intraperitoneal injection of Arachlor 1254 (500 mg/kg). The S9 consisted of the 9000×G supernatant of liver homogenized in 0.25 M sucrose-100 mM phosphate buffer (pH 7.4) (Molecular Toxicology, Inc.). Cofactors were 1 mM NADP and 5 mM sodium isocitrate. On the day of exposure, cultures of cells, with or without the metabolism mixture, were incubated for 4 hours in RPMI containing 5% FBS and graded doses of BTO956, 964, 966, or 967. The test agents were prepared in serial dilutions from 10 mM stock solutions in DMSO yielding a dose range 100 $\mu$M, 50 $\mu$M, 25 $\mu$M, 10 $\mu$M and 5 $\mu$M concentrations and a final DMSO concentration of 1%. In each case, cells were maintained at 37° C. under 5 percent $CO_2$ in air. The experiments were conducted in 6-well tissue culture plates (Falcon) with an initial seeding density of 2×10$^6$ cells per well in 2 ml aliquots. The test compounds were added immediately to the medium in duplicate cultures. Treatment solution was removed by a series of low-speed centrifugations to pellet the cells, followed by removal of the supernatant and resuspension of cells in fresh RPMI containing 10% FBS.

The results shown in FIG. 2 indicate that BTO-956 is metabolized within the 4-hr incubation period to an inactive form. These results also show that BTO-964 is more resistant to metabolic degradation and more toxic to HL60 cells than is BTO-956. In contrast, BTO-966 and BTO-967 appear to be activated to more cytotoxic products.

C. In vivo efficacy of BTO-964 and BTO-967 against met-1 mouse mammary tumors

Mammary fat pads of Balb/c immunodeficient (nude) mice were implanted with 1 mm$^3$ of mammary tumor tissue. These mammary tumors originated from the met-1 mouse mammary tumor cell line and have been propagated by passaging in vivo. When palpable tumors appeared, animals were subdivided into various treatment groups and treated daily with intraperitoneal injections of control vehicle, BTO-967 (50 mg/kg), or BTO-964 (50 mg/kg). A group of untreated control animals was included in the study, because agents used in the vehicle for these test articles (DMSO/ethanol/Cremophor EL/PEG 400, 1: 0.5 : 0.5: 6) were themselves found to have cytotoxic activity. Twice weekly, the volumes of the tumors in each animal in each group were measured to gather information on tumor growth (volume) as a function of type of treatment, dose, and time.

Mice implanted with Met-1 tumor breast xenografts showed a positive response to treatment with BTO-964 (Table 2). Primary tumors in the BTO-964-treated animal groups were significantly smaller (p=0.06) than the control vehicle-treated animals after 4 weeks of therapy. The mean tumor volume of the drug-treated vs. vehicle-treated animals at 4 weeks was 876±126 mm$^3$ vs. 1238±170 mm$^3$, respectively; the difference between the animals treated with BTO-964 and the untreated (no vehicle) animals was highly significant (p=0.01).

TABLE 2

In Vivo Efficacy of A Representative Candidate Drug In The Met-1 Syngeneic Murine Mammary Tumor Model

| Treatment | Tumor Volume (mm$^3$)[a] | Percent Reduction (re. None/re. Vehicle) |
| --- | --- | --- |
| None | 1570 ± 219[b] | na |
| Vehicle only | 1238 ± 170 | −21%/na |
| BTO-964 | 876 ± 126 | −44%/−29% |

[a]Tumor volumes measured 4 weeks post initiation of treatment
[b]SEM = standard error of the mean

III. ANTI-ANGIOGENIC PROPERTIES

A. The chick chorioallantoic membrane (CAM) assay

BTO-964 [methyl 3,5-diiodo-4(4'-methoxyphenoxy) benzaldehyde], and BTO-967 [methyl 3,5-diiodo-4(4'-methoxyphenoxy)-thiobenzoate] were tested in the CAm assay. The endpoint of the CAM assay was a quantiative determination of basement membrane biosynthesis by measuring the incorporation of $^{14}$C-proline into Type IV collagenous protein.

The CAM assay involves the development of live chick embryos in Petri dishes under special sterile conditions. Therefore, only limited numbers of embryos can be used for evaluation of compounds in a single experiment. BTO-964 and BTO-967 was tested in separate assays. A known angiogenesis inhibitor, 2-methoxyestradiol (2-ME), was used as the positive control, and human fibroblast growth factor (hFGF) was used to induce angiogenesis in the CAM.

Fertilized eggs were supplied by Melody Ranch, Aptos, Calif. L-[U-$^{14}$C ] proline (specific activity, 290 mCi/mmol) was purchased from New England Nuclear, Boston, Mass. Collagenase and 2-ME were obtained from Sigma Chemical Co., St. Louis, Mo. Silicone ring cups were obtained by cutting silicone tubing (3 mm diameter) into small "O" rings 1 mm in thickness. These silicone ring cups can be reused many times if they are sterilized prior to each assay. Plastic Petri dishes (20×100 mm) were purchase from Baxter diagnostics, Inc., Hayward, Calif. hFGF-B was obtained from Clonetics Corporation, San Diego, Calif.

For testing, a minimum amount of acetone-methanol (1:1) was added to the test compounds for sterilization. The acetone-methanol mixture was then evaporated to dryness in a sterile hood. The compounds were dissolved in dimethyl sulfoxide (DMSO) first and then diluted with saline containing methylcellulose. The final concentrations were 2% DMSO and 0.5% methylcellulose. all test solutions were added to each CAM in 20-ml aliquots.

The method of Folkman, et al. (Folkman, et al. (1974) Dev. Biol. 41:391–394) with some modifications, was used to cultivate chicken embryos as follows:

Fresh fertile eggs were incubated for three days in a standard egg incubator. On Day 3, eggs were cracked under sterile conditions and embryos were placed in 20×100 mm plastic Petri dishes and cultivated at 37° C. in an embryo incubator with a water reservoir on the bottom shelf. Air was continuously bubbled into the water reservoir by using a small pump so that the humidity in the incubator was kept constant. Observations were made daily to ensure that all embryos were healthy. Dead or unhealthy embryos were removed from the incubator immediately to avoid contamination. On Day 9, a sterile silicone ring cup was placed on each CAM and 0.5 mCi of $^{14}$C-proline with or without the test compound plus 2.5 ng of hFGF dissolved in saline containing 0.5% methylcellulose was delivered into each ring cup in a sterile hood. 2-ME was tested in parallel to serve as a reference compound. After addition of test materials, the embryos were returned to the incubator and cultivation continued. On Day 12, all embryos were transferred to a cold room at 4–10° C. The antiangiogenic effect of each test compound was determined by using the collagenase assay to measure $^{14}$C-proline incorporation into collagenous protein.

B. Collagenase Assay for Measurement of $^{14}$C-Proline Incorporation into Collagenous Protein Using the procedure outlined in Maragoudakis, et al., (1989) J. Pharm. Exp. Ther. 251:679–682, the embryos were placed on ice and a piece of CAM 10 mm in diameter was cut off under each ring cup and placed in a separate tube. To each tube was added 1.0 ml of phosphate-buffered saline (PBS, pH 7.3) containing 0.11 mg cycloheximide and 0.17 mg dipyridyl. The tubes were placed in a boiling water bath for 10 min and then cooled to room temperature. The PBS in each tube was discarded after centrifugation at 3000×G for 10 min. The CAM residue was washed once with 3 ml of 15% TCA and then three times with 3 ml of 5% TCA. Centrifugation was carried out as described above between each washing. At this point all non-protein bound radioactivity was removed, and the CAM containing the newly synthesized $^{14}$C-collagenous protein was suspended in 0.9 ml of 0.1 N NaOH and 1.1 ml of HEPES buffer at pH 7.4. The pH of the sample was neutralized with 0.8 N HCl, using phenol red as indicator.

To digest the $^{14}$C-collagenous protein, 7.5 units of collagenase and 500 nmol of calcium chloride in 40 ml of HEPES buffer was added to the above samples, and mixtures were incubated at 37° C. for 4 h. The reaction was stopped by adding 1.0 ml of 20% TCA containing 5 mg of tannic acid into each tube. After vortex mixing, the samples were centrifuged at 3000×G for 10 min. An aliquot of the clear supernatant was taken for scintillation counting to quantitate the radiolabeled tripeptides corresponding to basement membrane collagen and other collagenous materials synthesized by the CAM from $^{14}$C-proline. The CAM pellets in each tube were solubilized in 0.5 ml of 1.0 N NaOH by boiling in a water bath for 5 min. An aliquot of the dissolved CAM was used for protein determination using the method provided by Pierce Chemical Co. The radioactivity per milligram of protein from the CAM treated with a test compound relative to that from the control CAM gave the percent of angiogenesis inhibition.

Tables 1 and 2 summarize the results of the two separate experiments. The results from these two experiments indicate that there is an antiangiogenic effect of BTO-967 and BTO-964 in the CAM assay.

TABLE 1

Inhibitory Effects of Biosource Compounds on Angiogenesis Induced by hFGF-B

| Compound | Dose (μg/CAM) | $^{14}$C-Proline Incorporated into Collagenous Protein (cpm/mg_protein) (mean ± S.E.) | % Inhibition |
| --- | --- | --- | --- |
| BTO-967 | 75 | 5581 ± 1182 | 11 |
|  | 25 | 6165 ± 1288 | 3 |
|  | 8.3 | 5222 ± 692 | 13 |

TABLE 1-continued

Inhibitory Effects of
Biosource Compounds on Angiogenesis Induced by hFGF-B

| Compound | Dose (µg/CAM) | $^{14}$C-Proline Incorporated into Collagenous Protein (cpm/mg_protein) (mean ± S.E.) | % Inhibition |
|---|---|---|---|
| 2-Methoxyestradiol | 75 | 3875 ± 891 | 38 |
|  | 25 | 5068 ± 1609 | 20 |
|  | 8.3 | 5711 ± 1469 | 9 |
| Control | — | 6300 ± 696 | — |

TABLE 2

Inhibitory Effects of
Biosource Compounds on Angiogenesis Induced by hFGF-B

| Compound | Dose (µg/CAM) | $^{14}$C-Proline Incorporated into Collagenous Protein (cpm/mg_protein) (mean ± S.E.) | % Inhibition |
|---|---|---|---|
| BTO-964 | 75 | 10076 ± 928 | 10 |
|  | 25 | 8121 ± 1096 | 27 |
|  | 8.3 | 9526 ± 1492 | 15 |
| 2-Methoxyestradiol | 75 | 6984 ± 1022[b] | 38 |
|  | 25 | 7303 ± 1424 | 35 |
|  | 8.3 | 10499 ± 1372 | 6 |
| Control | — | 11200 ± 829 | — |

[b]Significantly lower than control, P < 0.01.

IV. ASSAYS USED TO SCREEN FOR ANTI-MITOTIC PROPERTIES

A. Microtubule Assembly Inhibition Assays

A cell-free assay for measuring inhibition of the microtubule assembly can be performed by first mixing tubulin and rhodamine-labeled tubulin at a ratio of 4:1 (Hyman, A., et al. (1990) *Meth. Enzymol.* 196, 478–485; Belmont, L. D., et aL (1996) *Cell* 84, 623–631). This tubulin solution is then added on ice to a buffer (BRB 80; 80 mM potassium salt of PIPES (pH 7.5), 5 mM $MgCl_2$, 1 mM EGTA) containing 1 mM GTP and 1 mM DTr top a 15 µM final concentration. Drugs at different concentrations (0.5 µl) are added to 50 µl samples of the buffered tubulin, and 10 µl of each solution is transferred to microfuge tubes. Each tube receives 0.4 µl of microtubule seeds (Belmont, L. D., supra). Tubes are incubated at 37° C. for 10 min before adding 100 µl of BRB 80 containing 1% glutaraldehyde. Each reaction mixture (2.5 µl) is transferred to a microscope slide for fluorescence microscopy.

Microtubules in intact cells are visualized by using a mouse anti-α-tubulin monoclonal antibody and a fluorescein-labeled donkey anti-mouse polyclonal antibody. Briefly, HeLa cells are plated in 2-well chamber slides (Nunc, Napierville, Ill.) at $1.5 \times 10^4$/ml and incubated in 5% $CO_2$ at 37° C. for 24 h before treatment with drugs for 1 h. After removing the medium, cellular microtubules are stabilized by using BRB 80 containing 4 mM EGTA and 0.5% Triton X-100. The cells are fixed for 3 min in methanol chilled at −20° C., washed with TBS buffer (0.15 M NaCl, 0.02 M Tris-HCl, pH 7.4), and permeabilized with TBS/ 0.5% Triton X-100. After several washes with TBS/0.1% Triton X-100, the cells are blocked with an antibody dilution buffer (TBS, 0.1% Triton X-100, 2% BSA, 0.1% sodium azide) for 10 min. The cells are stained in the dark with the primary antibody for 1.5 h, and then the secondary antibody is added in the antibody dilution buffer containing 1 µg/ml Hoechst 33342 and incubated in the dark for 45 min. The slides are mounted with n-propyl gallate (2% w/v in 30% 0.1 M Tris/glycerol, pH 9.0) and sealed under glass coverslips.

B. Competitive Tubulin-Binding Assays

The competitive binding of a compound to the colchicine binding site of tubulin is performed by using a spin column method (Woods, J. A., et al. (1995) *British J. Cancer* 71, 705–711). $^{14}$C-labeled BTO-956 (20 µM, 10 nCi) is mixed with tubulin and colchicine at different concentrations and incubated at room temperature for 1.5 h in a buffer containing 0.1 M MES (pH 6.8), 1 mM EGTA, 1 mM EDTA, and 1 mM $MgCl_2$. Each reaction mixture is loaded onto a column containing 1 ml of Sephadex G50 equilibrated with a buffer containing 40 mM MES (pH 7.5), 40 mM Tris, and 1 mM $MgSO_4$. The columns are centrifuged at 900×G for 3 min and the eluents are each mixed with 3 ml of CytoScint (ICN) for analysis by liquid scintillation counting.

V. USE OF THE COMPOUNDS AS SENSITIZERS FOR RADIOTHERAPY

A. In vitro Radiosensitization Assay

Radiosensitization studies are performed on cancer cells grown in culture. The test compound is added to the cells prior to, during, or after irradiation. Radiation dosages are typically measured in units of Gy/min, with one Gy is equal to 100 rads, while one rad is the quantity of ionizing radiation that results in the absorption of 100 ergs of energy per gram of irradiated material. Sensitization enhancement ratios (SER) are determined at a 10% survival level. The $C_{1.6}$ value (i.e., a concentration of test compound yielding an SER of 1.6) is determined by plotting SER values against test compound concentration.

HeLa S-3 cells are grown and maintained in modified Eagles's medium containing 10% fetal bovine serum in a humidity and $CO_2$-controlled incubator. Experimental studies are initiated on exponential cultures growing in 60 mm tissue culture dishes at treatment densities of 3–7×10<5> cells/dish. The doubling time of HeLa S-3 cultures is typically approximately 18 hours.

A compound of formula (I) is dissolved in distilled water just prior to use and diluted 1:100 through addition of the appropriate volume to cultured cells. For ultraviolet irradiation studies, compound is added only during the repair period following irradiation. For X-irradiation studies, drug is added to cultures 1 hour prior to irradiation and remains in contact with cells during irradiation.

For ultraviolet (non-ionizing) irradiation, al medium is removed from cultures and, with the lid removed, dishes are exposed to 1.4 $J/M^2$ of UV254 nm light emitted from a G.E. germicidal lamp. Fresh media with or without test compound is then added to cultures during the subsequent repair period. In some cases, cells are harvested immediately in order to establish a $T_0$ value for DNA strand breaks. X-irradiation (ionizing) of cultures is carried out in a TFI Bigshot X-ray unit at 3 mA, 50 keV, filtered with 1.5 mm Be and delivering 0.56 Gy/min to the cells (through the lid and 5 mls of media) as determined by a Victoreen ionization chamber calibrated in the 10 to 50 keV range. Following X-irradiation, cultures are harvested immediately for colony forming ability assays. $D_0$ values are calculated from survival curves computer plotted by linear regression analysis.

The ability of cells to form colonies after irradiation is determined by standard methods. Cultures treated with test compound are irradiated and immediately trypsinized, counted and replated in 5 ml medium containing the appropriate number of cells (500 for untreated cultures and cultures exposed to 2.8 Gy X-rays; 2,000 for cultures exposed to 20 J/M$^2$ UV; 5,000 for cultures exposed to 5.6 Gy X-rays and 10,000 for cultures exposed to 8.4 Gy X-rays). Cultures are grown for 10 days at which time colonies of 1.0–2.0 mm (50–200 cells) are evaluated by methanol fixation and staining. Untreated HeLa cells exhibit cloning efficiencies in the range of 34 to 46% using this protocol.

B. In vivo Radiosensitization Assay

This example describes one method by which one of skill in the art can assay the effect of the compounds of the invention on radiotherapy of malignant tumors. The model system used in this study is well established for determining the effects of radiation on tumor tissue. See, e.g., Twentyman, et al. (1980) *J. Nat'l. Cancer Inst.* 64: 595–603; Brown, et al. (1980) *J. Nat'l. Cancer Inst.* 64: 603–611; Bernstein, et al. (1982) *Radiation Res.* 91: 624–637. The model uses RIF-1 tumor cells, which are well suited to studies of radiation response, including in vitro cell survival and in vivo tumour studies, in part because of its rapid growth rate, with a doubling time of 65 hours and a cell cycle time of 12 hours. The RIF-1 tumour is minimally immunogenic, and metastasizes only at a late stage of growth.

Tumors are produced by the subcutaneous inoculation into the lower backs of mice. This inoculation consists of a suspension of 2×10$^5$ RIF-1 cells from culture in 0.25 ml of alpha minimum essential media (MEM, Gibso) supplemented with 10% fetal bovine serum (Johns Scientific). Male C3H/He mice (Harlan Sprague Dawley Inc., Indianapolis, Ind.) that are 5 to 7 weeks old at the time of inoculation are suitable for these experiments. Animals are anaesthetized for the inoculation.

The tumors are then allowed to grow to 1 cm in average diameter. Measurements are made using a caliper, talking the tumour length and width and calculating the average of these two. Tumour diameter measurements are taken every 2 to 3 days from the time the tumor cells were implanted.

Tumors are allowed to grow to approximately 1 cm average diameter without any intervention. Upon the tumors reaching this average diameter, the subject animals are randomized into one of three groups. One group receives no radiation and no test compound, a second group receives radiation and no test compound, and a third group receives radiation and test compound.

For radiation treatment, each animal receives a general anaesthetic. Animals immobilized and placed in the radiotherapy apparatus for the same period of time. The radiation exposure consists of a single dose of 3000 cGy of 150 KeV X-irradiation (mean time 10 minutes, 40 seconds). Preferably, the radiotherapy equipment (Protea ionization chamber) is calibrated before and after each session to ensure absolute uniform dosing. The radiotherapy is administered with a cone over the tumour and lower back of the animal, which in every case assures a uniform maximal delivery dose to the tumour while minimizing dose delivery to the sensitive structures of the abdomen and upper pelvis.

Those animals randomized to the test compound-treated group receive an intravenous dose of a compound of Formula I.

The day the subject animal is treated is designated Day Zero. At frequent intervals, usually every other day, the tumors are measured in the same fashion as previously described, and an average of two diameters calculated. These data are plotted as a function of time. The end-point of the study occurs when the tumor reaches double the original treatment diameter, or approximately 2 cm. Animals are euthanized in a $CO_2$ chamber and the tumors removed surgically post-mortem. Representative tumors are sectioned, paraffin embedded and slides are stained using H&E stain and examined to confirm the histological presence of RIP-1 fibrosarcoma. Animals are sacrificed and tumors harvested before the tumor reaches twice the original diameter in the following situations: premature death of animal following treatment; ulceration of the tumor; or infection or inflammation of the injection site.

Following the termination of the experiment, growth curves for each subject tumor are completed and a line of best fit assigned for purposes of interpolation between data points. The average diameter (AD) of each tumor is then determined for each day of the study from the lane of best fit.

VI. USE OF THE COMPOUNDS AS SENSITIZERS FOR CHEMOTHERAPY

Assays for determining appropriate dosages of the compounds of the invention for use as sensitizers for chemotherapy and immunotherapy are similar to those described for radiotherapy. To examine the "preincubation effect" of the compounds of the invention, cancer cells are exposed to a fixed concentration of a test compound for 2 hours, followed by exposure to varying concentrations of a chemotherapeutic or immunotherapeutic agent for 1 hour at 37° C., and then assayed for colony formation. In evaluating the effect of "preincubation time" on chemosensitization, cancer cells are exposed to fixed concentrations of the test compound for 0 to 4 hours at 37° C., followed by exposure to a chemotherapeutic agent under aerobic conditions for 1 hour at 37° C., and then assayed for colony formation. Test compound dose-dependent potentiation also is examined by exposing cancer cells to various test compound concentrations for 2 hours at 37° C., and then to a fixed dose of each chemotherapeutic agent for 1 hour at 37° C. under aerobic conditions. Experiments using a simultaneous addition of the sensitizer and chemotherapeutic agent for 1 hour at 37° C. under aerobic conditions can also be performed.

VII. CHEMOPREVENTION

The efficacy of the claimed compounds as a chemopreventive agent can be demonstrated using in vitro and in vivo models of 5AzadC-induced carcinogenesis. A suitable model system uses premalignant murine fibroblasts (cell lines 4C8 and PR4) that express a transcriptionally activated c-Ha-ras protooncogene. These non-tumorigenic cells, which are highly susceptible to malignant conversion by pharmacological doses of 5AzadC, are subclones of mouse NIH 3T3 fibroblasts, PR4N and 4C8-A10 (designated here PR4 and 4C8) and have been previously described (see, e.g., Wilson, et al. (1986) *Anal. Biochem.*, 152: 275–284; Dugaiczyk (1983) *Biochem.* 22:1605–1613). Both cell lines are phenotypic revertants isolated from LTR/c-Ha-ras1-transformed 3T3 cells after long-term treatment with murine interferon alpha/beta. Cultures are maintained in Dulbecco's modified Eagle's medium (DM supplemented with 10% heat inactivated fetal calf serum (Gibco) and antibiotics. The sodium salts of phenylacetic and phenylbutyric acids (Elan Pharmaceutical Corporation) are dissolved in distilled water. 5AzadC (Sigma St. Louis, Mo.) is dissolved in phosphate buffered saline (PBS) and stored in aliquots at −20° C. until use. Exposure of 5AzadC to direct light is avoided at all times to prevent drug hydrolysis.

For in vitro tests, cells are plated at $1-2\times10^5$ cells in 100 mm dishes and the test compound added to the growth medium at 20 and 48 hrs later. The cells are subsequently subcultured and observed for phenotypic alterations. Whereas untreated 4C8 and PR4 form contact-inhibited monolayers composed of epithelial-like cells, transient exposure of these cultures to 0.1 μM 5AzadC during logarithmic phase of growth results in rapid and massive neoplastic transformation. Within one week of 5AzadC treatment, the great majority of the cell population become refractile and spindly in shape, and form multilayered cultures with increased saturation densities, which is indicative of loss of contact inhibition of growth. Treatment of the cells with the test compound reduces or prevents these phenotypic changes. The test compound can be administered prior to treatment of the cells with 5AzadC, simultaneously with 5 AzadC treatment, or after 5AzadC treatment.

For in vivo tests of the ability of the test compounds to prevent malignancy, 6–9 week-old female athymic nude mice are inoculated subcutaneously (s.c.) with $0.5\times10^6$ cells. Twenty four hours later 400 μg of freshly prepared 5AzadC in 200 μl PBS is administered intraperitoneally (i.p.) into each animal (approximately 20 mg/kg). The test compound is also administered to the animal. The number, size, and weight of tumors is recorded after 3–4 weeks. For histological examination, tumors are excised, fixed in Bouin's solution (picric acid: 37% formaldehyde: glacial acetic acid, 15:5:1 vol/vol), and stained with H&E. A single i.p. injection of mice with 5AzadC (20 mg/kg) typically results in tumor development at the site of 4C8 cell inoculation in controls. However, animals protected by a compound of the invention either fail to develop tumors or form slow-growing lesions at the site of 4C8 inoculation.

An additional test of the ability of the compounds of the invention to prevent malignant growth involves inhibition of cell growth on matrigel, which is a reconstituted basement membrane (Collaborative Research). This assay models the ability of cells to degrade and cross tissue barriers. Cells are exposed for 48 hrs in plastic tissue culture dishes with 5AzadC alone or in combination with the test compound. Treatment with the test compound is continued for an additional 1–2 weeks, after which cells are replated onto 16 mm dishes that were previously coated with 250 μl of matrigel (10 mg/ml). The test compound is either added to the dishes or omitted in order to determine whether the effect is reversible. In the absence of test compound, net-like formation characteristic of invasive cells typically occurs within 12 hours, and invasion into the matrigel is evident after 6–9 days.

VIII. ASSAY FOR MEASURING THE ABILITY OF COMPOUNDS OF FORMULA I TO REDUCE THE LEVELS OF TUMOR NECROSIS FACTOR (TNF-α).

This example provides an assay that can be used to screen compounds of Formula I for their ability to reduce the expression of cytokines (e.g., TNF-α) in a mammal.

A. Materials and Methods

1. Cell line

The murine macrophage PU5-1.8 cell line are purchased from the American Type Culture Collection (ATCC, Rockville, Md.). Cells are grown in DMEM medium supplemented with 100 mM sodium pyruvate, 0.1 mM nonessential amino acids, 2 mM glutamine and 5 % fetal bovine serum (Life Technologies, Staten Island, N.Y.). Cells are maintained in a humidified atmosphere of 5% $CO_2$-95% air at 37° C. Cells are passaged twice weekly by firmly tapping the side of the flask to dislodge the adherent cells. Both nonadherent and adherent cells are passaged. Exponentially growing cells are seeded at $5\times10^5$/mL, 4 mL per 60-mm dish 24 h prior to the experiment. Test compounds are delivered in 1 mL volumes of the medium added to each dish at the start of the experiment. All dishes are incubated at 37° C. in 5% $CO_2$-95% air for 3 h.

2. Reagents.

The Tumor Necrosis Factor (TNF-α) cDNA is obtained from the ATCC (Rockville, Md.). [α-$^{32}$P]-dCTP (250 μCi) and nylon membranes (Hybond N) are obtained from Amersham (Arlington Heights, Ill.). Colchicine (used as a control) is purchased from the Sigma Chemical Company (St. Louis, Mo.). Lipopolysaccharide (LPS) from *Escherichia coli* is purchased from DIFCO Laboratories (Detroit, Mich.). All plastic supplies are purchased from VWR Scientific products (San Francisco, Calif.).

3. Northern blotting

Total RNA is isolated by the guanidinium-cesium chloride method as described in N. S. Waleh, J. Gallo, T. D. Grant, B. J. Murphy, R. H. Kramer and R. M. Sutherland, (1994) "Selective downregulation of integrin receptors in spheroids of squamous cell carcinoma," *Cancer Res.*, 54:838–843. Five to 10 μg of total RNA is electrophoresed in 1% agarose gels containing 6% formaldehyde. Following electrophoresis, gels are stained with ethidium bromide to visualize the positions of 28S and 18S RNA. The RNAs is then transferred to nylon membranes (Amersham Hybond N) by capillary blotting and fixed to the filter by exposure to UV light. The blots are probed with $^{32}$P-labeled cDNA sequences of human TNF-α obtained from the American Type Culture Collection (ATCC). The TNF-α cDNA is a 1.1 kb PstI fragment of plasmid pE4 in *E. coli* MM294 (ATCC 39894). Hybridizations is carried out at 42° C. in 50% formamide, 5 X SSC, 5X Denhardt's solution, 0.1% SDS, and 0.3 mg/mL salmon sperm DNA. Filters are washed by 1 X SSC, 0.1% SDS, twice at room temperature for 15 min and once at 55° C. in 0.1 X SSC, 0.1% SDS for 1 hr. Filters are exposed to X-ray film at −70° C. using an intensifying screen (Coronex Hi-Plus).

Hybridized bands are quantified by analyzing the images obtained by using a video densitometer (Applied Imaging Corporation, Santa Clara, Calif.). Film densities are calibrated using an optical-density wedge.

Treatment of PU5-1.8 murine macrophages with LPS (100 ng/mL) for 3 h resulted in a significant increase (>7 fold) in the level of TNF-α mRNA as determined by Northern blot analysis. Treatment of cells with colchicine at 10 μM concentration had no effect on TNF-α mRNA expression. However, addition of colchicine at 10 μM to the LPS treated cultures resulted in substantial reduction of TNF-α mRNA accumulation. The inhibition levels were 68% for colchicine.

To establish a concentration-effect relationship, macrophages are exposed to various concentrations of compounds of Formula I in the presence of the stimulus LPS for 3 h. The amounts of TNF-α mRNA declines with increasing concentrations of the compounds of Formula I. The compounds of Formula I that were tested were statistically as effective as colchicine at downregulating TNF-α. Thus, the above assay can be used to show that compounds of Formula I have the ability to reduce the level of TNF-α produced by a cell.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method of inhibiting the growth of a tumor cell, said method comprising contacting said tumor cell with a compound having the structure:

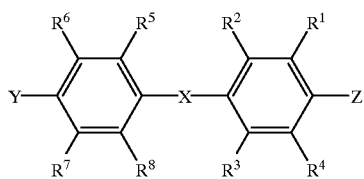

or a pharmaceutically acceptable salt thereof;
wherein:
X, if present, is a member selected from the group consisting of

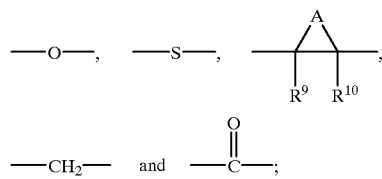

A, together with the carbons to which it is bound, forms an optionally substituted 3, 4, 5 or 6 membered carbocylic or heterocyclic ring; $R^9$ and $R^{10}$ are members independently selected from the group consisting of hydrogen, alkyl and halogen; Y is a member selected from the group consisting of H, alkyl and alkoxy;

Z is a member selected from the group consisting of

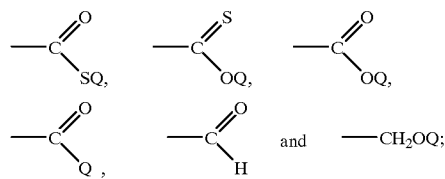

Q is a member selected from the group consisting of H, alkyl and S-alkyl;

$R^1$, $R^2$, $R^3$ and $R^4$ are members independently selected from the group consisting of H, alkyl, alkenyl, alkynyl, aryl, hydroxyl, alkoxy, halogen, nitro and amino; and $R^5$, $R^6$, $R^7$ and $R^8$ are members independently selected from the group consisting of H, alkyl, alkenyl, alkynyl, hydroxyl, alkoxy and halogen;

with the proviso that if Z is

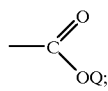

and Q is methyl, then Y is other than methoxy and ethoxy.

2. The method in accordance with claim 1 wherein
X is —O—;
Y is methoxy;
Z is

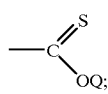

Q is methyl;
$R^1$ and $R^4$ are both hydrogen;
$R^2$ and $R^3$ are both iodo; and
$R^5$, $R^6$, $R^7$ and $R^8$ are all hydrogen.

3. The method in accordance with claim 1 wherein
X is —O—;
Y is hydrogen;
Z is

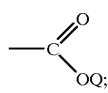

Q is methyl;
$R^1$ and $R^4$ are both hydrogen;
$R^2$ and $R^3$ are both iodo; and
$R^5$, $R^6$, $R^7$ and $R^8$ are all hydrogen.

4. The method in accordance with claim 1 wherein
X is —O—;
Y is alkyl;
Z is

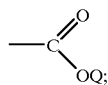

Q is methyl;
$R^1$ and $R^4$ are both hydrogen;
$R^2$ and $R^3$ are both iodo; and
$R^5$, $R^6$, $R^7$ and $R^8$ are all hydrogen.

5. The method in accordance with claim 1 wherein
X is —O—;
Y is methoxy;
Z is

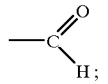

$R^1$ and $R^4$ are both hydrogen;
$R^2$ and $R^3$ are both iodo; and $R^5$, $R^6$, R7 and $R^8$ are all hydrogen.

6. The method in accordance with claim 1 wherein
X is —O—;
Y is methoxy;
Z is —CH$_2$OQ;
Q is hydrogen;
$R^1$ and $R^4$ are both hydrogen;
$R^2$ and $R^3$ are both iodo; and
$R^5$, $R^6$, $R^7$ and $R^8$ are all hydrogen.

7. The method in accordance with claim 1 wherein
X is —O—;
Y is methoxy;
Z is —CH$_2$OQ;
Q is methyl;
$R^1$ and $R^4$ are both hydrogen;
$R^2$ and $R^3$ are both iodo; and
$R^5$, $R^6$, $R^7$ and $R^8$ are all hydrogen.

8. The method in accordance with claim 1 wherein said compound is selected from the group consisting of

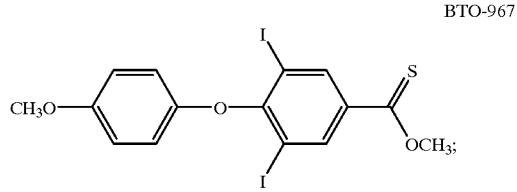
BTO-967

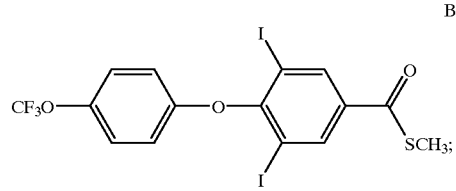
BTO-969

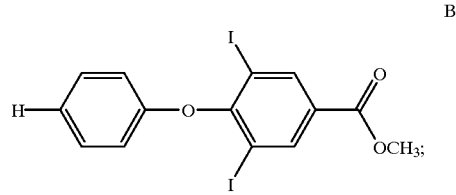
BTO-990

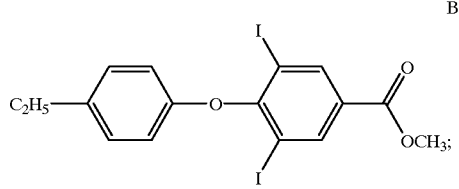
BTO-971

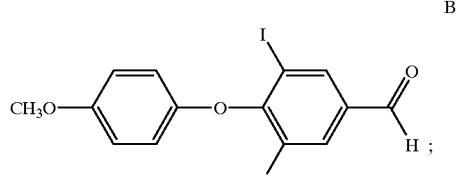
BTO-964

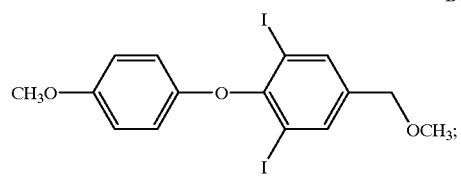
BTO-966

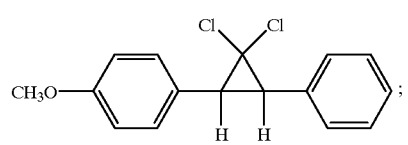
BTO-980

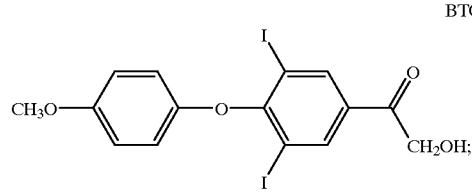
BTO-972

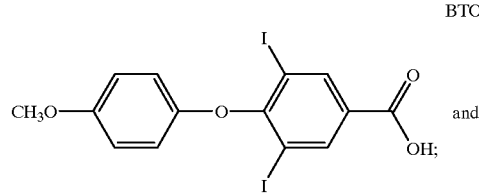
BTO-985

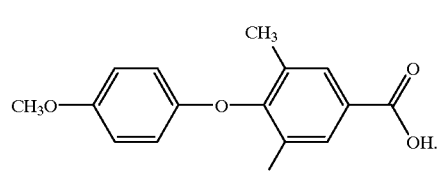
BTO-986

9. The method in accordance with claim 1 wherein said tumor cell is selected from the group consisting of lung, colon, breast, ovarian, prostate and hepatic cells.

10. The method in accordance with claim 1 wherein said tumor cell is in a mammalian subject.

11. The method in accordance with claim 1 wherein said tumor cell is a squamous cell carcinoma.

12. The method in accordance with claim 1 wherein said compound is formulated in a pharmaceutically acceptable form with an excipient or carrier.

13. The method in accordance with claim 1 wherein said compound is formulated in a liposome.

14. The method in accordance with claim 1 wherein said compound is administered orally.

15. The method in accordance with claim 1 further comprising the step of observing for a reduction in the growth of said tumor cell.

16. A method of inhibiting the growth of a tumor cell in a mammalian subject, said method comprising administering to said subject a therapeutically effective amount of a compound having the structure:

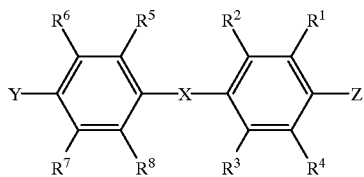

or a pharmaceutically acceptable salt thereof;
  wherein:
    X, if present, is a member selected from the group consisting of

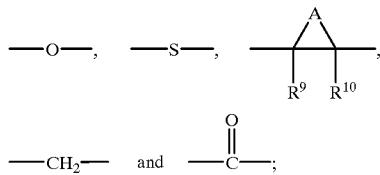

A, together with the carbons to which it is bound, forms an optionally substituted 3, 4, 5 or 6 membered carbocylic or heterocyclic ring; $R^9$ and $R^{10}$ are members independently selected from the group consisting of hydrogen, alkyl and halogen; Y is a member selected from the group consisting of H, alkyl and alkoxy;

Z is a member selected from the group consisting of

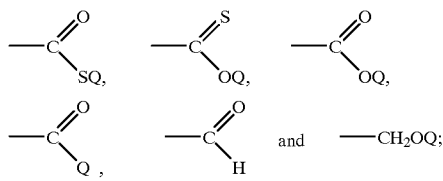

Q is a member selected from the group consisting of H, alkyl and S-alkyl;

$R^1$, $R^2$, $R^3$ and $R^4$ are members independently selected from the group consisting of H, alkyl, alkenyl, alkynyl, hydroxyl, alkoxy, halogen, nitro and amino; and $R^5$, $R^6$, $R^7$ and $R^8$ are members independently selected from the group consisting of H, alkyl, alkenyl, alkynyl, hydroxyl, alkoxy and halogen;

with the proviso that if Z is

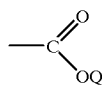

and Q is methyl,
  then Y is other than methoxy and ethoxy.

17. A method of inhibiting the growth of a tumor cell in accordance with claim 16 wherein said administration is carded out in combination with immunotherapy.

18. A method of inhibiting the growth of a tumor cell in accordance with claim 17, further comprising the step of administering to said mammal a tumor vaccine.

19. A pharmaceutical composition comprising a pharmaceutically acceptable carrier and a compound having the structure:

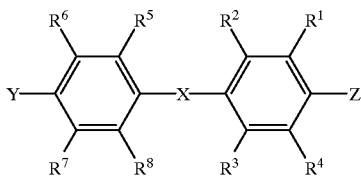

or a pharmaceutically acceptable salt thereof;
  wherein:
    X, if present, is a member selected from the group consisting of

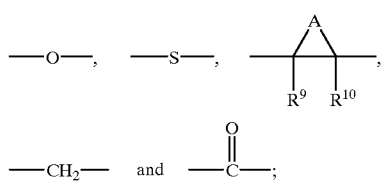

A, together with the carbons to which it is bound, forms an optionally substituted 3, 4, 5 or 6 membered carbocylic or heterocyclic ring; $R^9$ and $R^{10}$ are members independently selected from the group consisting of hydrogen, alkyl and halogen; Y is a member selected from the group consisting of H, alkyl and alkoxy;

Z is a member selected from the group consisting of

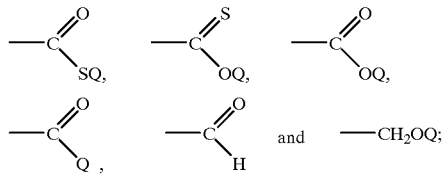

Q is a member selected from the group consisting of H, alkyl and S-alkyl;

$R^1$, $R^2$, $R^3$ and $R^4$ are members independently selected from the group consisting of H, alkyl, alkenyl, alkynyl, hydroxyl, alkoxy, halogen, nitro and amino; and $R^5$, $R^6$, $R^7$ and $^8$ are members independently selected from the group consisting of H, alkyl, alkenyl, alkynyl, hydroxyl, alkoxy and halogen;

with the proviso that if Z is

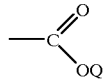

and Q is methyl,
  then Y is other than methoxy and ethoxy.

20. The pharmaceutical composition in accordance with claim 19 wherein
  X is —O—;
  Y is methoxy;

Z is

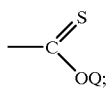

Q is methyl;
R¹ and R⁴ are both hydrogen;
R² and R³ are both iodo; and
R⁵, R⁶, R⁷ and R⁸ are all hydrogen.

21. The pharmaceutical composition in accordance with claim 19 wherein
X is —O—;
Y is hydrogen;
Z is

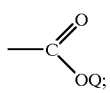

Q is methyl;
R¹ and R⁴ are both hydrogen;
R² and R³ are both iodo; and
R⁵, R⁶, R⁷ and R⁸ are all hydrogen.

22. The pharmaceutical composition in accordance with claim 19 wherein
X is —O—;
Y is alkyl;
Z is

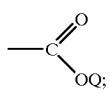

Q is methyl;
R¹ and R⁴ are both hydrogen;
R² and R³ are both iodo; and
R⁵, R⁶, R⁷ and R⁸ are all hydrogen.

23. The pharmaceutical composition in accordance with claim 19 wherein
X is —O—;
Y is methoxy;
Z is

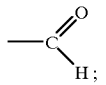

R¹ and R⁴ are both hydrogen;
R² and I³ are both iodo; and
R⁵, R⁶, R⁷ and R⁸ are all hydrogen.

24. The pharmaceutical composition in accordance with claim 19 wherein
X is —O—;
Y is methoxy;
Z is —CH₂OQ;
Q is hydrogen;
R¹ and R⁴ are both hydrogen;
R² and R³ are both iodo; and
R⁵, R⁶, R⁷ and R⁸ are all hydrogen.

25. The pharmaceutical composition in accordance with claim 19 wherein
X is —O—;
Y is methoxy;
Z is —CH₂OQ;
Q is methyl;
R¹ and R⁴ are both hydrogen;
R² and R³ are both iodo; and
R⁵, R⁶, R⁷ and R⁸ are all hydrogen.

26. The pharmaceutical composition in accordance with claim 19 wherein said compound is selected from the group consisting of

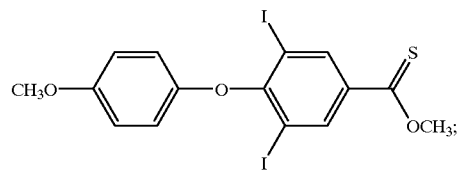
BTO-967

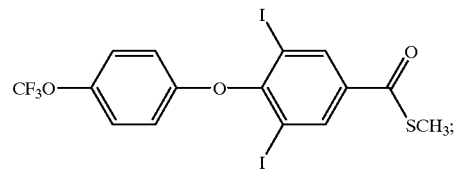
BTO-969

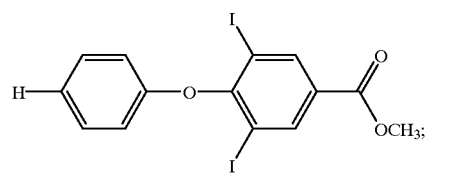
BTO-990

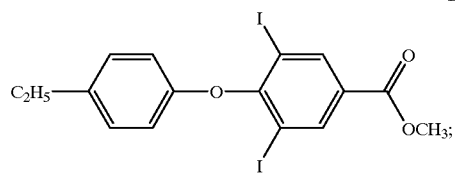
BTO-971

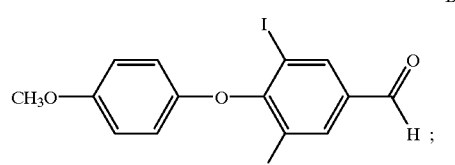
BTO-964

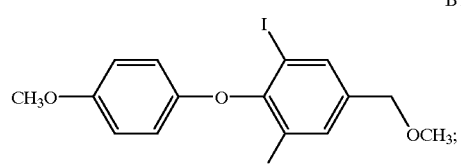
BTO-966

BTO-980
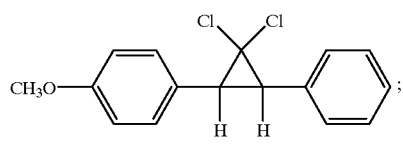
BTO-972
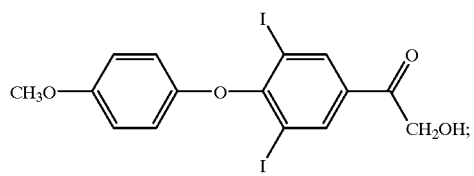
BTO-985
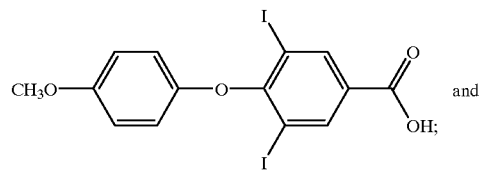
and
BTO-986
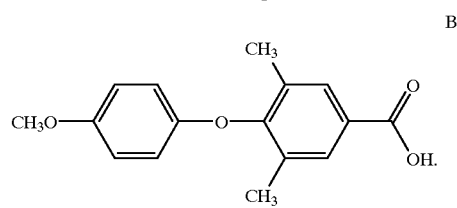
* * * * *